United States Patent
Strnad et al.

(10) Patent No.: US 10,076,373 B2
(45) Date of Patent: Sep. 18, 2018

(54) SELF-RETAINING FASTENER AND DRIVER

(71) Applicant: Intrepid Orthopedics, Richfield, OH (US)

(72) Inventors: Lee A Strnad, Richfield, OH (US); Christopher S Lorkowski, Olmsted Township, OH (US); Adam A Barlett, Streetsboro, OH (US)

(73) Assignee: INTREPID ORTHOPEDICS, Richfield, OH (US)

( * ) Notice: Subject to any disclaimer, the term of this patent is extended or adjusted under 35 U.S.C. 154(b) by 671 days.

(21) Appl. No.: 14/645,726

(22) Filed: Mar. 12, 2015

(65) Prior Publication Data
US 2015/0257807 A1 Sep. 17, 2015

Related U.S. Application Data

(60) Provisional application No. 61/988,932, filed on May 6, 2014, provisional application No. 61/951,601, filed on Mar. 12, 2014.

(51) Int. Cl.

| | |
|---|---|
| *A61B 17/68* | (2006.01) |
| *A61B 17/86* | (2006.01) |
| *B25B 23/10* | (2006.01) |
| *B25B 15/00* | (2006.01) |
| *A61F 2/30* | (2006.01) |
| *A61B 17/84* | (2006.01) |
| *A61B 17/88* | (2006.01) |
| *A61F 2/46* | (2006.01) |

(52) U.S. Cl.
CPC ........ *A61B 17/8615* (2013.01); *A61B 17/888* (2013.01); *A61B 17/8888* (2013.01); *B25B 15/005* (2013.01); *B25B 23/105* (2013.01); *A61B 17/84* (2013.01); *A61B 17/861* (2013.01); *A61B 17/864* (2013.01); *A61B 17/866* (2013.01); *A61B 17/88* (2013.01); *A61B 17/8875* (2013.01); *A61F 2002/305* (2013.01); *A61F 2002/30504* (2013.01); *A61F 2002/4638* (2013.01)

(58) Field of Classification Search
CPC . A61F 2002/30378; A61F 2002/30479; A61B 17/861–17/862
See application file for complete search history.

(56) References Cited

U.S. PATENT DOCUMENTS

| | | | |
|---|---|---|---|
| 7,846,167 B2 * | 12/2010 | Garcia | A61B 17/862 606/104 |
| 2003/0074003 A1 * | 4/2003 | Deslauriers | A61B 17/861 606/308 |

(Continued)

OTHER PUBLICATIONS

McTighe, T. et al, Metallic Modular Taper Junctions in Total Hip Arthroplasty, Reconstructive Review, Jul. 2015, pp. 29-42, vol. 5, No. 2, Joint Implant Surgery & Research Foundation, Chagrin Falls, Ohio, USA.

*Primary Examiner* — Yashita Sharma
*Assistant Examiner* — Rebecca Preston
(74) *Attorney, Agent, or Firm* — Brainspark Associates, LLC

(57) ABSTRACT

A provisional engagement feature for selectively connecting a fastener such as a screw to a driving tool, the fastener incorporating a head with a recess extending therein and a projection contained within the recess for engagement with a corresponding engagement feature of the driving tool.

20 Claims, 28 Drawing Sheets

(56) References Cited

U.S. PATENT DOCUMENTS

| | | | |
|---|---|---|---|
| 2005/0119747 A1* | 6/2005 | Fabris Monterumici | ................... A61B 17/025 623/17.11 |
| 2008/0039844 A1* | 2/2008 | Jackson | ............. A61B 17/7037 606/266 |
| 2011/0066187 A1* | 3/2011 | Fang | .................. A61B 17/7002 606/254 |
| 2012/0253467 A1* | 10/2012 | Frankle | ..................... A61F 2/40 623/19.11 |
| 2013/0030476 A1* | 1/2013 | Shimko | .............. A61B 17/8615 606/308 |
| 2014/0081333 A1* | 3/2014 | Jackson | ............. A61B 17/7031 606/257 |

\* cited by examiner

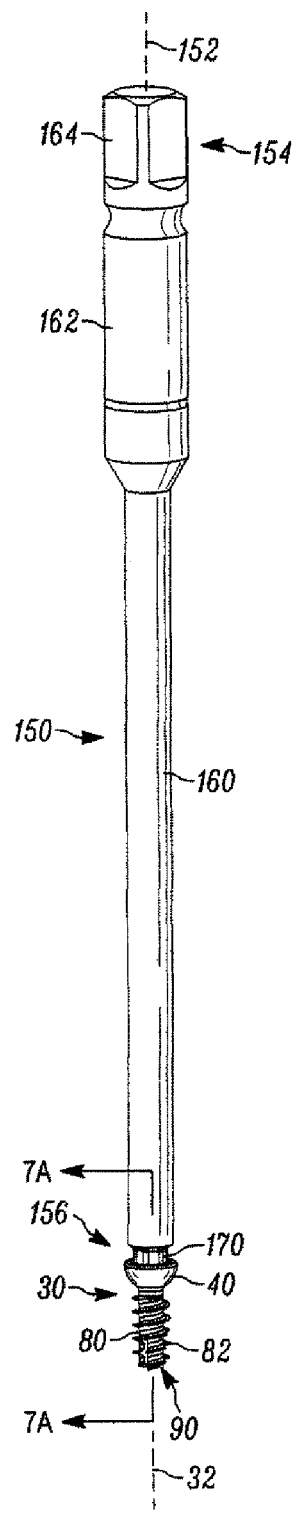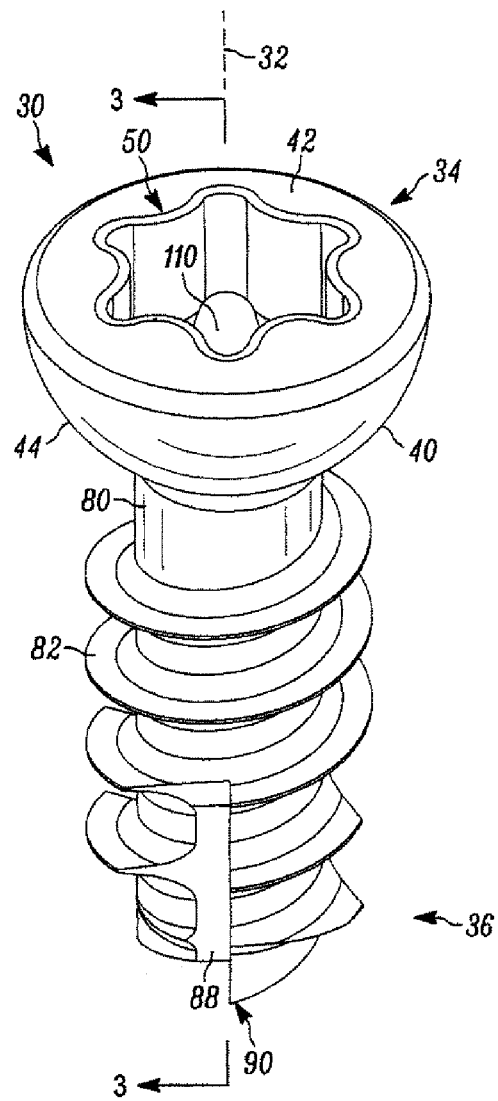
FIG. 1
FIG. 2

SELF-RETAINING FASTENER AND DRIVER

CROSS-REFERENCE TO RELATED APPLICATIONS

This application claims the benefit of U.S. Provisional Patent Application Ser. No. 61/951,601 entitled "Self-Retaining Screw and Driver," filed Mar. 12, 2014, and U.S. Provisional Patent Application Ser. No. 61/988,932 entitled "Self-Retaining Screw and Driver," filed May 6, 2014. The disclosure of these documents are each incorporated by reference herein in their entireties.

TECHNICAL FIELD

The present invention relates generally to fasteners and, in particular, relates to a self-retaining fastener and fastener driver for installing the fastener into a structure or work piece for use in a variety of industries, including, but not limited to, construction, engineering, manufacturing and medical treatment applications.

BACKGROUND

Fasteners are used to secure a multitude of different components and materials together for a variety of applications including, but not limited to, assembling and securing manufacturing components, connecting building materials such as metal, polymer, plastic or wood, and the use of fasteners for attachment to biological materials such as bone and/or soft tissue during medical treatment procedures. In many cases, fasteners can include a generally cylindrical body having an external thread (i.e., a thread-based fastener or "screw"), in which a generally cylindrical screw body is formed separate from an associated driving or fixating tool (i.e., a "driver"), with the driver removed from the screw once the securing operation is completed (and the screw is left behind in the construct or work piece). There is a constantly increasing number and variety of applications for the use of screw-based fasteners, but one consistent need encountered in many applications is a desired for the driver to temporarily "hold," center and/or otherwise retain and/or secure the fastener (i.e., to the driver) prior to and/or during the securing operation into the particular material and/or structure, yet which allows the driver to be quickly and easily removed from the fastener once the connection operation is completed. This is especially true where the driver requires two hands to manipulate and/or operate, where it may be advantageous for an individual to use one hand for the driver and the other to hold the work piece accepting the fastener, and where a dropped and/or lost screw can cause unintended damage and/or long term consequences (i.e., during a medical procedure and/or during aircraft engine repair).

In the biomedical field, an increasing number of applications are being developed which involve the use of mechanical fastener constructs that are surgically implanted to allow the body to mend or be reconstructed (i.e., temporarily and/or permanently). Such applications can include fasteners used with spinal constructs and disk replacements, plates used for long bone repair from the femur to the metacarpals, and even soft tissue repairs such as tendon and ligamentoplasty, as well as bladder and hernia repair. In many instances, a surgeon may only have a single hand free to operate the driver (or the surgical field may not allow for more than a single hand and/or the driver tip to penetrate the patient and/or the surgical field). Moreover, a fastener that unintentionally dislodges or otherwise "drops" into a wound can cause significant damage to the patient as well as potentially become "lost" within the wound—often with long term consequences for the patient.

There are many orthopedic surgical and dental procedures in which a fastener is implanted to hold bone in a certain position and/or to provide an anchor for a dental or other prosthetic or implant. In small bone surgery (e.g., below the elbow and ankle), the available fastener products are typically scaled-down versions of larger fasteners used for larger bones, and these versions are often not adequate for the fine bones and delicate procedures required of the small bone surgeon. In particular, the small bones are often fine and have minimal surface area for placement of an implant, and typically less mass for placement of a screw-type fastener. In addition, there is usually minimal soft tissue in the regions to "cover" and/or cushion an implant. These factors tend to make small bone surgery particularly tedious and unforgiving. Consequently, it is desirable to have surgical tools for small bone surgery that provide assistance in holding, centering and/or implanting the delicate screw that are used in this areas of the body—especially where the design allows fewer "hands" to be involved in the procedure and does not significantly increase the dimensions and/or "profile" of the screw head.

SUMMARY OF THE INVENTION

In accordance with various aspects of the present invention, a fastener, such as a screw-type fastener, includes a proximal end and a distal end, with a shaft or other body extending at least partially from the proximal end to the distal end. The shaft desirably includes an externally threaded portion for securing the fastener to a structure with a driving, fixating or placement tool. The fastener desirably includes a head incorporating a driving feature located at the proximal end, the head having an axial end surface and a recessed portion including an axially extending first inner surface within the recess. The recess desirably extends from the axial end surface towards a distal end of the fastener, with the first inner surface including at least one projection or other feature extending proximally from the first inner surface, the projection being sized and/or configured to engage with a corresponding engagement feature of the driving or placement tool. In various embodiments, the engagement between the projection and the engagement feature is a friction fit, while in other embodiments the engagement can comprise a detent-type mechanism or a positive locking-type fit.

In accordance with another aspect of the present invention, a screw and screwdriver combination includes a screw extending along an axis and having a proximal end and a distal end. A head located at the proximal end has an axial end surface and an axially extending first inner surface defining a recess. The recess extends from the axial end surface towards the distal end of the screw and terminates at a second inner surface. Optionally, a projection may extend from the second inner surface towards the axial end surface and terminate at a proximal extent. The projection has an engagement feature, such as a friction fit, detent-type mechanism or a positive locking-type fit with a tool. A shaft extends from the head and incorporates a thread for securing the screw into a work piece with the tool. The screw further includes a shaft extending from the head and having a thread for securing the screw in a structure/work piece. A screwdriver extends along an axis and has a proximal end and a distal end. A handle is located at the proximal end of the screwdriver and a shaft extends distally from the handle. A pilot located at the distal end of the screwdriver can cooperate with the first inner surface of the screw.

In accordance with another aspect of the present invention a surgical screw has a proximal end and a distal end. The screw includes a head located at the proximal end and having an axial end surface and an axially extending first inner surface that defines a recess. The recess extends from the axial end surface towards the distal end of the screw and terminates at a second inner surface. A projection extends from the second inner surface towards the axial end surface and terminates at a proximal extent. The projection has an engagement feature that provisionally engages the projection with a corresponding feature of a tool. A shaft extends from the head and has a thread for securing the screw in bone with the tool.

In accordance with another aspect of the present invention a surgical screw and screwdriver combination includes a surgical screw extending along an axis and having a proximal end and a distal end. A head located at the proximal end has an axial end surface and an axially extending first inner surface defining a recess. The recess extends from the axial end surface towards the distal end of the screw and terminates at a second inner surface. A projection extends from the second inner surface towards the axial end surface and terminates at a proximal extent. The screw further includes a shaft extending from the head and having a thread for securing the screw in bone. A screwdriver extends along an axis and has a proximal end and a distal end. A handle is located at the proximal end of the screwdriver and a shaft extends distally from the handle. A pilot located at the distal end of the screwdriver cooperates with the first inner surface of the screw. The pilot has an inner surface that forms an engagement feature with the projection of the screw.

BRIEF DESCRIPTION OF THE DRAWINGS

The foregoing and other objects, aspects, features, and advantages of embodiments will become more apparent and may be better understood by referring to the following detailed description of the preferred embodiments, taken in conjunction with the accompanying drawings, wherein:

FIG. 1 is a schematic illustration of a self-retaining fastener and fastener driver in accordance with an aspect of the present invention;

FIG. 2 is an isometric view of the fastener of FIG. 1;

DETAILED DESCRIPTION

Figure 3:
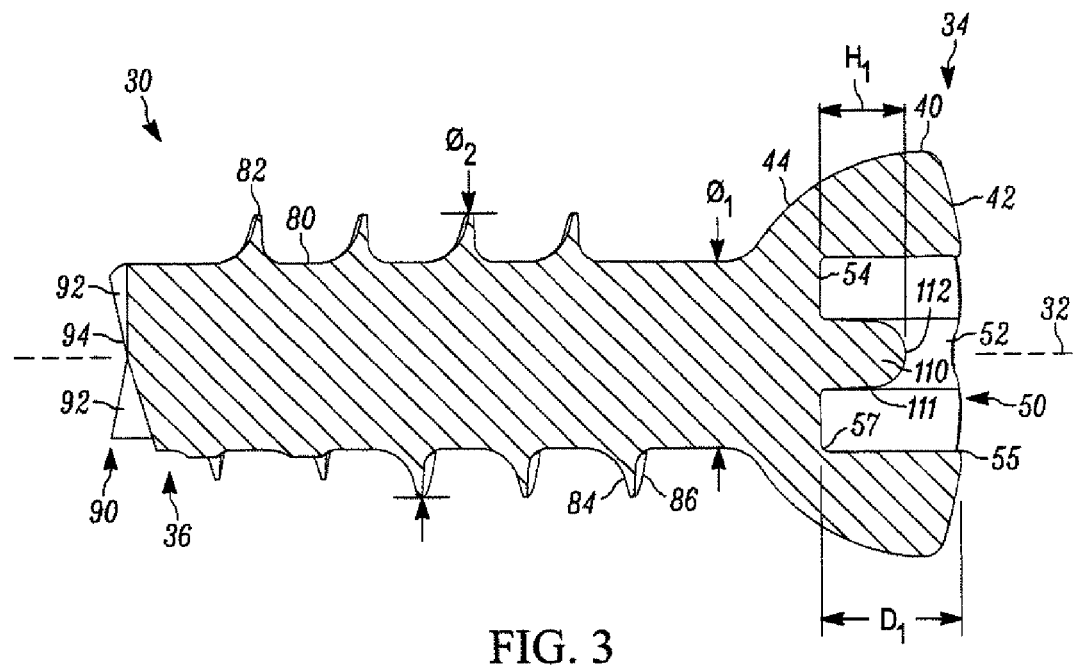
FIG. 3 is a sectional view taken along line 3-3 of FIG. 2.

Various features of the present invention include the recognition of a need for a more effective system of provisionally connecting a fastener, such as a screw-based or other type of fastener, to a driving or placement tool, thereby allowing the fastener to be carried and/or positioned solely by manipulation of the tool, and then attached or introduced into a work piece by actuation of the tool, with the tool being quickly and easily detached from the fastener once the fastener is in a desired position. A variety of configurations, sizes and shapes of such fasteners and associated tools can be utilized in diverse environments, which can range from construction and manufacturing to use in surgery and medical procedures. In various medical applications, the disclosed fasteners and related tools and techniques can desirably facilitate the use of various fasteners by surgeons, which can be important to achieve the most accurate and best performance and/or fit of implant components.

It will be apparent that a fastener and associated fastening tool with a provisional engagement system such as described herein can provide a number of attendant advantages, including the ability to "preload" a fastener onto a tool, which allows the tool to be freely manipulated with one or both hands and the fastener utilized without concern that the fastener will unintentionally separate from the tool. Similarly, the provisional engagement systems described herein can allow a fastener to be removed from a work piece, with the fastener desirably retained by the removal tool (and then easily removed from the tool by a user), which can obviate dropped and/or lost used fasteners and facilitates quick and easy fastener removal and disposal.

In various embodiments, the ability to provisionally engage a fastener to a driving tool can significantly reduce the opportunity for damaging the fastener due to insufficient contact between the fastener head and the driving bit during the installation and/or removal procedure (i.e., "stripping out" of the fastener head). Similarly, the various features described herein can reduce and/or eliminate the tendency for a fastener to "wobble" in the driving tool during initial placement of the fastener (i.e., various embodiments can "self-center" the fastener on the tool), which can prolong the life of the fastener and/or the driving tool, as well as significantly reduce the opportunity for unwanted damage to the work piece.

The present invention relates generally to fasteners and, in particular, relates to a self-retaining screw and screwdriver for installing the screw in a desired structure. The structure may comprise, for example, a substrate including a metal, polymer, plastic, ceramic, wood, bone or other biological tissue. In addition, while various embodiments herein describe a cylindrical screw body with externally-extending threads, a wide variety of other fastening arrangements known in the art could be utilized in combination with the various teachings provided herein, including, but not limited to, the use of twist-lock or expansion-type fasteners, machine-type fasteners, spring-loaded fasteners, rivets or virtually any other type of removable fastener and associated placement and/or driving tools.

FIG. 1 illustrates a self-retaining screw 30 and associated screwdriver 150 in accordance with an aspect of the present invention. The screwdriver 150 and screw 30 are desirably self-aligning and include one or more features that provide a friction fit or other selectable retention relationship between the screw and screwdriver, such that the screw remains provisionally connected to the screwdriver without requiring the operator to manually hold the screw onto the screwdriver.

Figure 4:
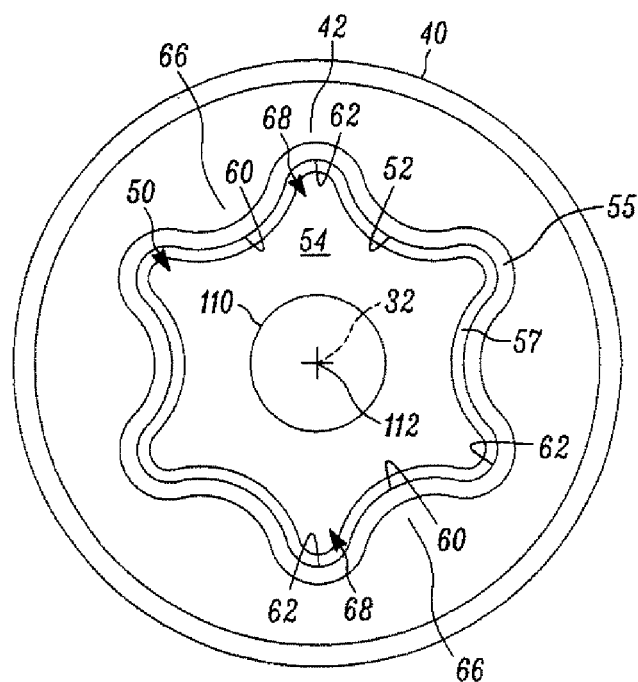
FIG. 4 is a top view of the fastener of FIG. 2.

Referring to FIGS. 2-4, the screw 30 has a first or proximal end 34 and a second or distal end 36. The screw 30 extends along an axis 32 and may be formed from any material, e.g., a metal, polymer or a biocompatible material. The screw 30 includes a head 40 and a shaft 80 extending from the head along the axis 32. The shaft 80 has an elongated shape with a circular cross-section having a diameter $\Phi_1$. Alternatively, the shaft 80 may taper inwardly in a direction extending towards the distal end 36 of the screw 30 (not shown). A thread 82 extends radially outward from the shaft 80. In one example, the thread 82 constitutes a cancellous thread having a substantially constant outer diameter $\Phi_2$. It will be appreciated, however, that the thread 82 may have alternative thread configurations, e.g., square, buttress, sawtooth, etc., and/or have a variable outer diameter $\Phi_2$ tailored for ease of manufacture, load carrying capacity, ease of use and/or securing the screw 30 to a particular structure and/or environment. The thread 82 in the disclosed embodiment forms a spiraling, helical pattern around and along the shaft 80 from a location adjacent the head 40 to the distal end 36 of the screw 30.

The distal end 36 of the screw 30 terminates at a cutting tip 90 formed by a plurality of sharp, angled flutes 92 collectively defining a recess 94. Alternatively, the distal end 36 of the screw 30 may terminate at a blunt tip (not shown). A recess 88 or "cutting tooth" (or other similar features) can be formed in the thread 82 and can extend approximately parallel to the axis 32 from the tip 90 towards the first end 34 of the screw 30. Alternatively, the thread 82 and the tip 90 may incorporate self-tapping characteristics and/or lead type screw designs. Such lead type screw designs, include single lead, dual lead, triple lead, and/or quad lead to affect their static or quasi-static performance, such as efficiency, driving torque requirements, increased number of engagement points and load capacity. The self-tapping characteristics may include thread-forming or thread cutting features, if desired.

Referring to FIG. 3, the head 40 of the screw 30 includes a generally axial end surface 42. A rounded surface 44 connects the axial end surface 42 to the shaft 40. The axial end surface 42 may be rounded, planar (not shown) or any other desired shape, with the screw head formed in almost any configuration, including square and/or hexagonal. The rounded surface 44 may be configured to mimic the contour of the structure to which the screw 30 is secured, and if desired may incorporate roughened and/or cutting surfaces to prepare and/or engage with underlying surfaces of the substrate. For medical applications, for example, the rounded surface may be configured to mimic the contour of an underlying bony surface to which the screw is secured, or the rounded surface may prepare the underlying bony surface and/or include surface features that can osseo-integrate with the bone surface, if desired. A recess 50 extends inward from the axial end surface 42 towards the shaft 80. The recess 50 can have a depth $D_1$ measured from the axial end surface 42 to a bottom or inner end surface 54 within the screw 30 or a plurality of such surfaces of varying depths is similarly contemplated by the present disclosure. The inner end surface 54 may be located within the head 40, as shown, or may be located within the shaft 80 (not shown), or may extend within both the head and shaft (not shown), if desired.

Referring to FIG. 4, the recess 50 in the disclosed embodiment is further defined and bounded by a generally longitudinally-extending inner surface 52 of the head 40. In the disclosed embodiment, the inner surface 52 is formed in a generally hexalobular shape that is positioned at a location generally symmetrical about the axis 32, but such positioning may be asymmetrical (not shown), if desired. The longitudinally-extending inner surface 52 of the disclosed embodiment is generally perpendicular to the inner end surface 54, but may taper inwards and/or outwards to varying degrees, if desired.

In the disclosed embodiment, the inner surface 52 desirably includes a plurality of first portions 60 and a plurality of second portions 62. Both the first and second portions 60, 62 are desirably arcuate or curved and are connected to one another in an alternating, end-to-end manner to encircle the axis 32. The first portions 60 have a convex shape and the second portions 62 have a concave shape. Each first portion 60 defines a lobe 66 extending radially towards the axis 32. The second portions 62 define spaces 68 between the lobes 66. Collectively, the lobes 66 and spaces 68 form and define a hexalobe, radially outer contour of the recess 50. Although six lobes 66 and six spaces 68 are illustrated in FIG. 4 it will be appreciated that the inner surface 52 may be configured to form more or fewer lobes and/or spaces in a symmetric or asymmetric pattern in accordance with the present invention. Furthermore, although the recess 50 is shown in FIG. 3 as having a larger cross-section than the shaft 80 it will be appreciated that the recess may have the same or a smaller cross-section than the shaft (not shown). It should also be understood that other recess shapes could be utilized in accordance with other embodiment of the present invention, including oval, triangular, square, pentagonal and hexagonal shapes (and so on), which may include straight and/or curved longitudinal surfaces in various combinations.

As best seen in FIG. 3, a rounded corner or fillet 55 can connect the inner surface 52 to the axial end surface 42. Similarly, a fillet 57 can be used to connect the inner surface 52 to the inner end surface 54. The use of fillets and similar machining techniques will desirably simplify manufacturing and/or machining of various components, as well as desirably reduce the opportunity for stress concentrations and/or notch sensitivity. It should be appreciated, however, that the inner surface 52 may be formed into a variety of planer and/or non-planar shapes, including shapes that alternatively taper inwards and/or outwards in a direction extending towards the distal end 36 of the screw 30.

Referring to FIGS. 3 and 4, an axially extending projection 110 extends from the inner end surface 54 away from the shaft 80. In this embodiment, the projection 110 is desirably spaced entirely from the inner surface 52. The projection 110 is centered on the axis 32 but may be offset or spaced from the axis (not shown). The projection 110 has a circular axial cross-section and a rounded side 111. The projection 110 desirably tapers inwardly in a direction extending from the inner end surface 54 towards the first end 34. The projection 110 terminates at a tapered, domed or hemispherical portion or surface defining a proximal extent 112 of the projection. The projection 110 has a height $H_1$ measured from the inner end surface 54 to the proximal extent 112. In the disclosed embodiment, the height $H_1$ is less than the depth $D_1$ of the recess 50, although in other embodiments the height $H_1$ of the projection 110 may be equal to and/or greater than the depth $D_1$ of the recess 50 (not shown).

Figures 5, 6A, 6B:
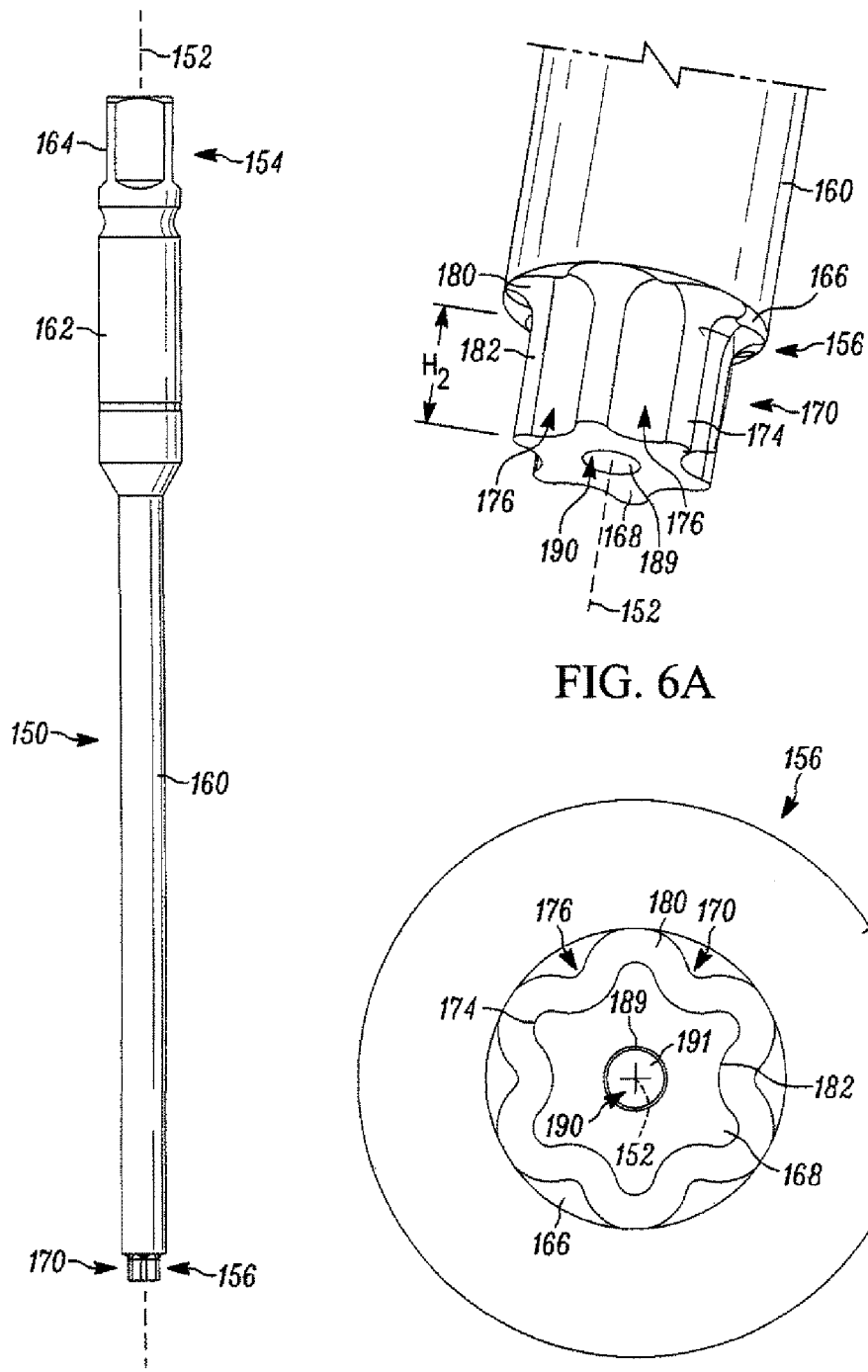
FIG. 5 is a side view of the fastener driver of FIG. 1.
FIG. 6A is an enlarged view of a portion of the fastener driver of FIG. 5.
FIG. 6B is a bottom view of the fastener driver of FIG. 5.

FIGS. 5-6B illustrate one exemplary embodiment of a placement tool such as a screwdriver 150, for use with the screw fastener 30 of the present invention. In this embodiment, the screwdriver 150 has a first or proximal end 154 and a second or distal end 156. The screwdriver 150 extends longitudinally along an axis 152 and includes an elongated body 160. A handle 162 extends proximally from the body 160. An adaptor 164 having a polygonal cross-section, e.g., square or hexagonal, extends proximally from the handle 162 along the axis 152. The adaptor 164 may be engaged by a tool (not shown) to facilitate operation of the screwdriver 150, or a handle or driving mechanism may be formed integrally therewith (not shown).

Referring to FIG. 6A, the distal end 156 of the screwdriver 150 of FIG. 5 desirably terminates at a post, boss or pilot 170, which desirably engages with the fastener. The pilot 170 fits into and cooperates with the recess 50 and projection 110 of the screw 30 such that the screw is desirably self-centering on the screwdriver and the pilot and screw are held together, with an engagement feature, such as a friction fit, detent-type mechanism or a positive locking-type fit, provisionally engaging between the screw and the screwdriver. This configuration also desirably seats the pilot 170 within the screw 30 so as to avoid having the pilot slide partially out of the recess and potentially stripping some or all of the interface between the screw and screwdriver 150. Desirably, the pilot 170 and projection 110 are sized and held to tolerance so that the engagement feature between the pilot and the screw 30 provides sufficient holding force to retain the screw on the screwdriver 150, without requiring the operator to manually hold the screw onto the screwdriver and/or limit movement and/or rotation of the screwdriver while the screw is provisionally attached thereto.

FIGS. 6A and 6B depict one embodiment of a lower portion of the body 160, which extends distally to an axial end surface 166. The pilot 170 comprises a projection which extends distally from the axial end surface 166. The pilot 170 desirably extends longitudinally along the axis 152 and terminates at an axial end surface or "tip" 168. In various embodiment, the pilot 170 may include a rounded or fillet portion 180 extending from the axial end surface 166, the incorporation of which will desirably simplify manufacturing and/or machining of various components, simply insertion of the pilot 170 into the recess, and desirably reduce the opportunity for stress concentrations and/or notch sensitivity to degrade and/or damage the tool. The pilot 170 further includes a portion 182 extending from the fillet portion a distal end surface 168. The portion 182 can have a height $H_2$, which can be measured from the fillet portion 180 to the axial end surface 168. In various embodiments, the height $H_2$ can corresponds to the depth $D_1$ of the recess 50 in the head 40 of the screw 30, although heights $H_2$ that may be lesser than or greater than the depth $D_1$ of the fastener are contemplated herein.

The portion 182 desirably includes a series of convex lobes 174 and concave spaces 176 between the lobes, with the lobes 174 and spaces 176 shown extending parallel to the axis 152. The lobes 174 of the pilot 170 are desirably sized and/or contoured to fit within the recess 50 of the fastener, desirably providing a slip fit engagement with the spaces 68 in the head 40 of the screw 30. Similarly, the spaces 176 between the lobes 174 are sized and contoured to form a slip fit engagement with the lobes 66 of the screw 30. Consequently, the portion 182 has a hexalobe axial cross-section, as disclosed herein, although various other tool shapes capable of fitting within and engaging some portion of the recess 50 of the fastener could be utilized (i.e., a dual lobe or tri-lobe pilot), with varying utility.

An inner surface 189 extends from the end surface 168 inwards towards the body 160 to define an opening 190, desirably configured to receive the projection 110 of the fastener or screw 30. The opening 190 is centered on the axis 152. In various embodiments, the opening 190 and projection 110 can desirably cooperate to center the pilot 170 within the recess 50 by aligning the axes 32, 152 of the screw 30 and screwdriver 150 when the two engage one another. The inner surface 189 is sized, shaped and configured to provide a provisional engagement between the tool and fastener, which in this embodiment comprises a friction fit between the inner surface 189 and the projection 110 on the screw 30, holding the fastener onto the tool such that a significant amount of translational and/or rotational movement can be transferred from the screwdriver 150 to the screw (when the pilot 170 is inserted within and engaged to the recess 50). Accordingly, in one exemplary embodiment the inner surface 189 can have a frustoconical shape, that desirably tapers inwardly in a direction extending from the end surface 168 towards the body 160, terminating at an axial end surface 191 (FIG. 6B). Of course, it is contemplated that the inner surface 189 may have a variety of shapes capable of engaging with the projection in a desired manner, including virtually any desired shape capable of providing the desired engagement function, e.g., cylindrical, including shapes that provide a friction fit with the projection 110. If desired, the inner surface 189 need not have a surface that exactly conforms to the outer surface of the projection 110.

Figure 7A:
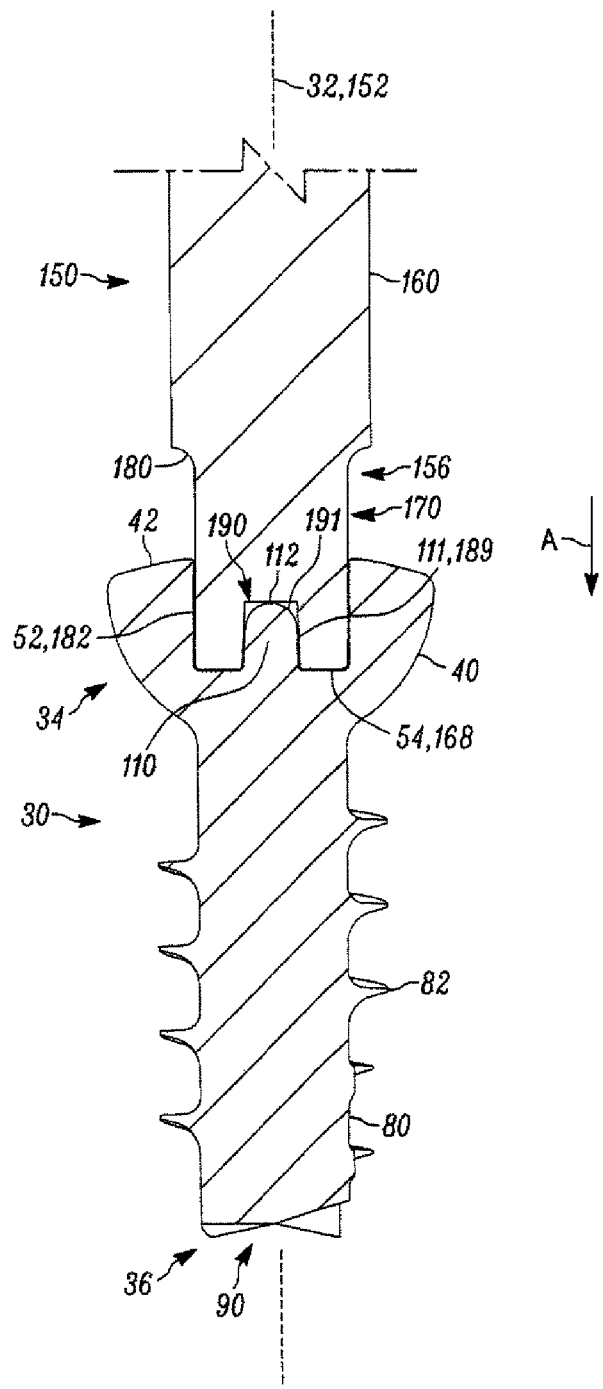
FIGS. 7A-7C are schematic views illustrating a method of installing the fastener of FIG. 2 in bone using the fastener driver of FIG. 5.
Figure 7B:
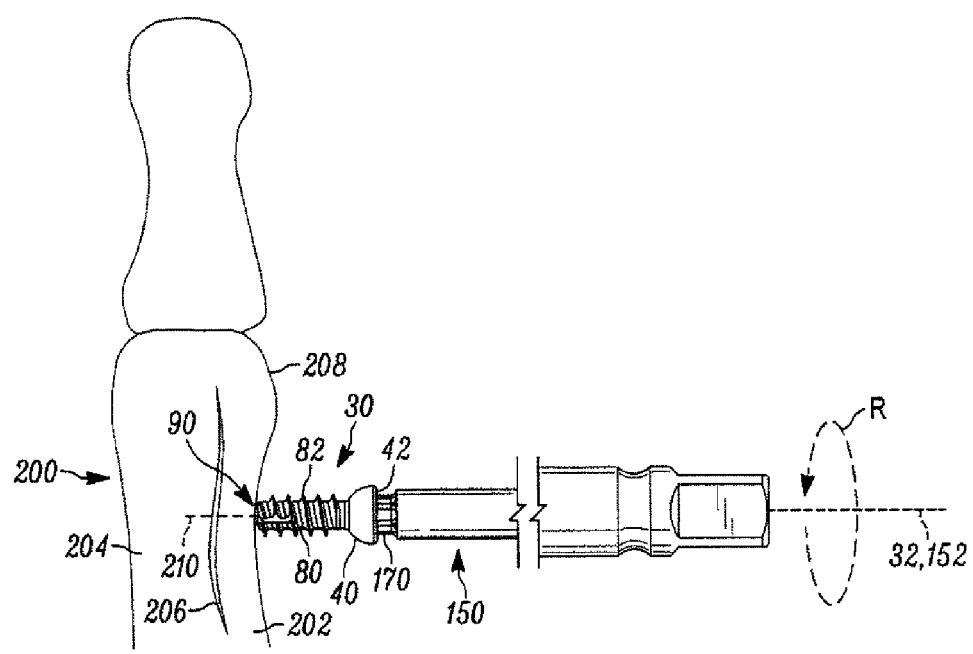
Figure 7C:
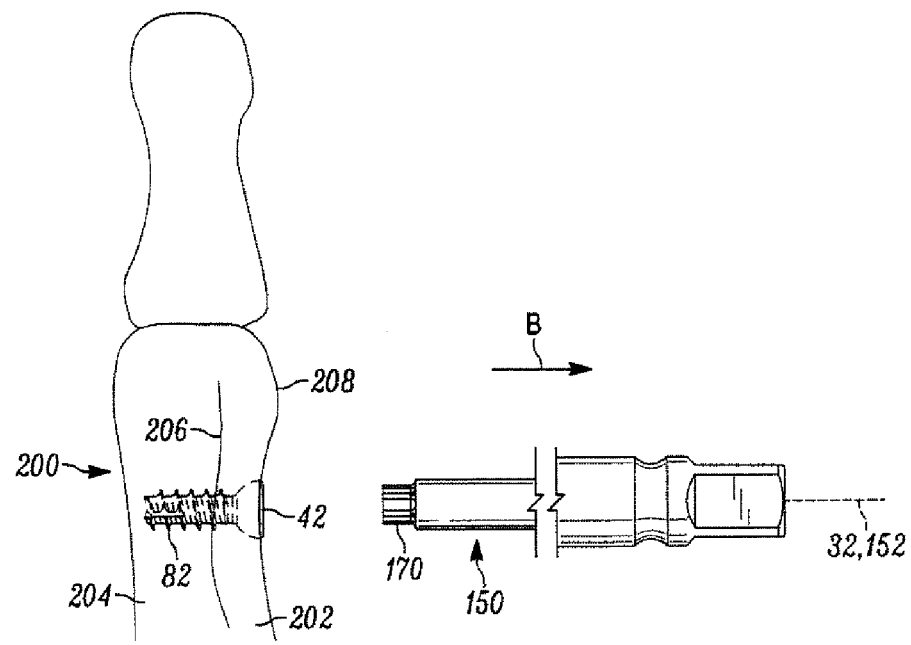

FIGS. 7A-7C illustrate one exemplary method of using the screw 30 and screwdriver 150 embodiments of the present invention. Although the method illustrates implanting the screw 30 within a metacarpal bone during a surgical procedure, it will be appreciated that the screw could likewise be utilized in virtually any other medical procedure requiring the use of fasteners, including implantation into any other small bone(s) in the body or used in a wide variety of other orthopedic and surgical applications including spinal surgery, plating in various areas of the body, soft tissue repair, bone anchoring or biological or artificial materials other than bone. It should also be appreciated that the fastener or screw could be utilized in a variety of non-medical applications, including in virtually any industry in which fasteners are currently used, including manufacturing and/or construction. If desired, the fastener could be secured to virtually any material, including metals, polymers, plastics, ceramics, stone, aggregates, composites and/or any other substance(s) normally fixated with fasteners.

Referring to FIG. 7A, the pilot 170 of the screwdriver 150 can be aligned with and inserted into the recess 50 in the screw 30. The axial cross-sections of the portion 182 and the recess 50 are desirably rotationally aligned with one another relative to the axes 32, 152 to allow the pilot to be inserted into the recess 50. This rotation can be accomplished by a user manually (i.e., by manually rotating a screw onto the non-rotating driver bit of the tool or by rotating the tool relative to the screw), or could be accomplished automatically using various alignment machinery or tools. The portion 182 and the recess 50 desirably help to self-center the screwdriver 150 and screw 30 to facilitate contacting and/or connecting the inner surface 189 and the projection 110. As noted, the portion 182 and the inner surface 52 are desirably configured to have a slip fit engagement with one another. Consequently, the portion 182 will optimally freely pass into the recess 50 once the pilot 170 and recess 50 are rotationally aligned with one another and the screwdriver 150 moved in the direction indicated generally by the arrow A into the recess.

Further movement of the screwdriver 150 in the direction A (relative to the screw) desirably causes the projection 110 to enter and become provisionally engaged (i.e., frictionally engaged or "wedged") with the inner surface 189. As disclosed in this embodiment, the frictional engagement between the projection 110 and inner surface 189 forms a friction fit. The friction fit connection securely retains the screw 30 on the pilot 170. In this configuration, the axial end surface 168 of the pilot 170 may engage the inner end surface 54 of the screw 30 or the pilot may be spaced from the inner end surface (not shown). If desired, some portion of the axial end surface 168 and/or fillet portion 180 might similarly engage with the axial end surface 42 of the screw (not shown), or the axial end surface 168 may be spaced from the axial end surface 42, as depicted in FIG. 7A. In the various embodiments, the advantageous friction fit and/or other engagement feature between the projection 110 and the inner surface 189 desirably permits a user of the tool (i.e., a surgeon, a machinist, an engineer, a construction worker, aircraft mechanic, etc.) to load and engage the screw with the driver tip of the tool, and subsequently freely manipulate the screw 30 on the screwdriver 150 (which may be accomplished in a single-handed operation, if desired) without being required to manually hold the screw onto the screwdriver.

Referring to FIG. 7B, the screw 30 and screwdriver 150 can be used to connect and/or secure together a first and second item or work piece, which in the figure is depicted as a first and second portions 202, 204 of a bone 200 having a fracture 206 therein. Once the screw 30 has been engaged and/or is friction fit onto the tip of the screwdriver 150 the cutting tip 90 of the screw 30 can be placed on an outer surface 208 of the bone 200 along a desired trajectory 210 through the bone 200. The desired trajectory 210 may traverse the first and second portions 202, 204 and the fracture 206. Rotation of the screwdriver 150 in the direction indicated by the arrow R about the axes 32, 152 desirably causes the cutting tip 90 to penetrate the bone 200 in a known manner. The configuration of the sharp flutes 92 and frustoconical recess 94 of the cutting tip 90 desirably causes the screw 30, upon rotation, to self-start and self-tap into the bone 200 along the trajectory 210. Continued rotation of the screwdriver 150 advances the screw 30 into the bone along the trajectory 210 until the axial end surface 42 of the head 40 is adjacent or substantially co-planar with the outer surface 208 of the bone 200 (FIG. 7C). This securely fixes the screw 30 in the bone 200 and desirably compresses the portions 202, 204 across the fracture 206 to facilitate healing of the fracture. The surgeon may then tilt and/or pull the screwdriver 150 away from the implanted screw 30 in a direction B to desirably release the engagement feature (i.e., frictional engagement in the disclosed embodiment) between the opening 190 and the projection 110. Engagement of the threads 82 within the bone 200 and/or other work piece desirably allows the user to impart a desired amount of force on the tool that imparts a separating force between the screw 30 and the screwdriver 150, which desirably overcomes the engagement force (i.e., friction fit) between the screw 30 and the screwdriver 150, allowing the tool to be removed from the screw without changing the position of the screw within the bone or other work piece and/or disturbing the work piece in an undesired manner. In one exemplary embodiment, the engagement force might be in the range of the weight of the fastener (or possibly 2, 3, 4, 5, 10 or 20 times the weight of the fastener), an ounce, a pound or more, while application of a greater amount of force than the engagement force (which may need to be applied in a particular direction, if desired) might easily separate the fastener from the driving tool.

FIGS. 8A-20D illustrate a variety of alternative configurations for fasteners that incorporate various provisional engagement features between the fastener and a fastening tool. In FIGS. 8A-20D, similar components for many features to those found in FIGS. 1-4 have been given the same reference numeral with the added suffix "a", "b", "c", "d", and "e", respectively. Although not shown or specifically described in many embodiments, it should be understood that an appropriate engagement feature of the fastening tool (i.e., the pilot of the screwdriver 150, for example) would desirably be appropriately contoured, shaped and/or sized to the shapes of the recess and/or projection (which could include identical configurations or non-identical configurations capable of engaging with corresponding features) in each of the alternative configurations of FIGS. 8A-20D. In various described embodiments, a corresponding opening inner surface and screw head projection could be designed to provide appropriate provisional engagement structures and their related relationships with each other, such as a friction fit, to provide similar or the same advantages as the screw 30 and screwdriver 150 of FIGS. 1-6B. Any of the screw configurations illustrated and described in the various figures contained herein may be configured for securing to any work piece and/or the aforementioned structures, e.g., a metal, polymer, plastic, wood, bone or other biological tissue.

Figure 8A:
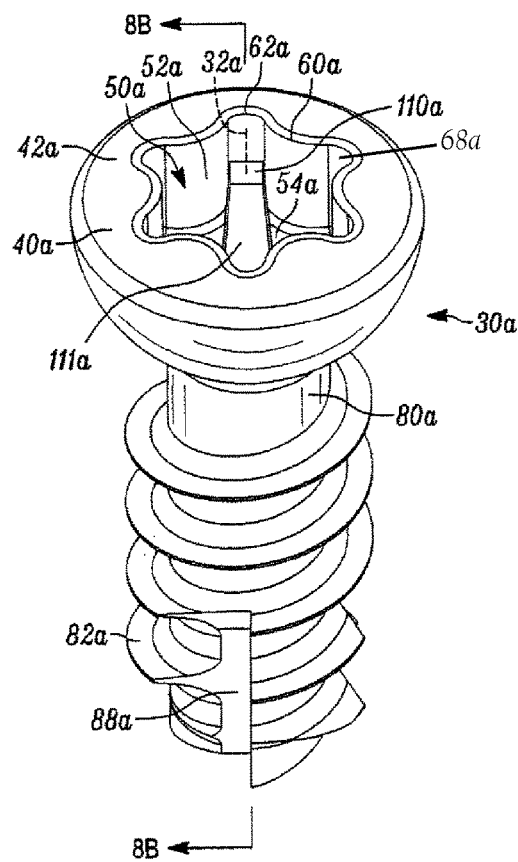
FIGS. 8A and 8B illustrate a fastener having an alternative configuration.
Figure 8B:
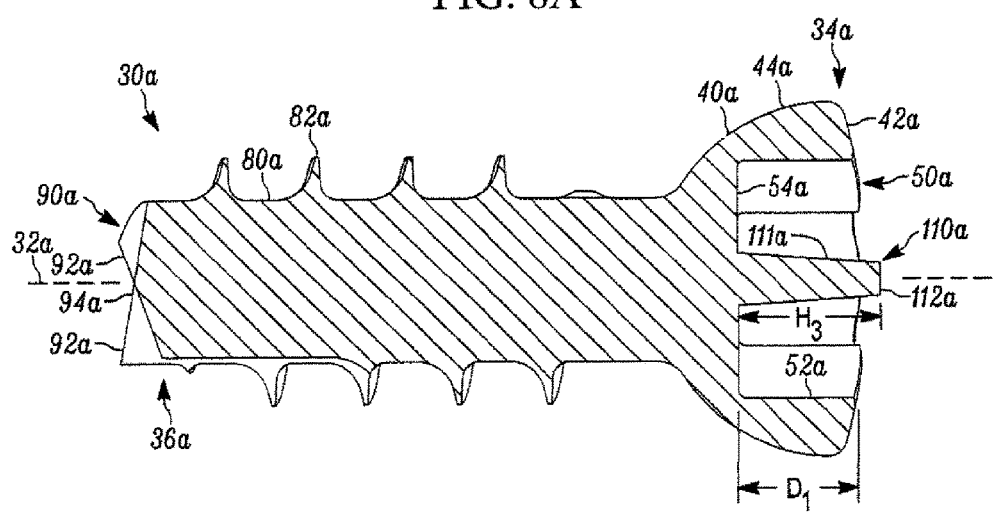

Referring to the embodiment of FIGS. 8A and 8B, a projection 110a can have a polygonal cross-section. In one example, the projection 110a can have a square or rectangular cross-section. The projection 110a has four sides 111a. It will be appreciated, however, that the projection 110a may constitute a different polygonal shape, e.g., oval, circular, triangular, hexagonal, etc. The projection 110a can taper continuously in a radially inward direction relative to the axis 32a as the projection extends from the inner end surface 54a towards the axial end surface 42a. Each of the sides 111a has a planar configuration but may alternatively have arcuate or curved contours (not shown). In this embodiment, the projection 110a extends axially beyond the axial end surface 42a of the head 40a. In other words, the height $H_3$ of the projection 110a measured from the inner end surface 54a to the proximal extent 112a is greater than the depth $D_1$ of the recess 50a. The height $H_3$ of the projection 110a may, however, be equal to or less than the depth $D_1$ of the recess 50 (not shown).

In various embodiments, it may be desirable that the projection include a number and/or distribution of external features (i.e., external surfaces and/or shapes) that match and/or correspond to the opposing inner surfaces of the recess (i.e., three or six projecting surfaces that match a hexalobe or hexagonal recess) to allow for the tool to assume a variety of rotational orientation relative to the fastener. Alternatively, the projection may provide for a limited number of orientations and/or only a single orientation of the tool relative to the fastener, if desired. In various embodiments, the projection may be provided with a particularized shape and/or size that corresponds to a specific use and/or fastening tool, such as where high-strength fasteners of a specific design and/or particularized fastening tools are desired for a particular application (i.e., aircraft fasteners and rivets). Similarly, the tool may include a feature that provides a particular rotational force that corresponds to a specific fastener—the projection could be particularized to only accept the desired torque tool or custom designed to incorporate a specific provisional engagement force. The projection may include user-defined engagement features to define the desired provisional engagement force or disengagement force. For example, if a projection includes a taper, the taper angle may be customized for light or heavy torque transmission loads. The taper angle may be adjusted to obtain an increased "frictional coupling," wedge or binding effect due to the friction across the entire surface area of the interface between the screwdriver or fastening tool and the screw and projection. Also, such custom engagement features may be designed to affect the provisional disengagement force. In various embodiment the disengagement force can be different than the engagement force. Potentially, the disengagement force may be so high that it may require a removal tool (i.e., a "drift", a drift punch, or a wedge, etc.) or an internal removal feature within the fastening tool. If desired, the torque tool could comprise a replaceable and/or modular bit or other driving feature that desirably fits into the fastening tool (i.e., a removable torque-limiting chuck).

Although not shown, it will be appreciated that an appropriate screwdriver 150 for use with the screw 30a of FIGS. 8A and 8B could be configured to cooperate with the screw 30a in a similar manner to how the screwdriver 150 cooperates with the screw 30 of FIGS. 2-4. In particular, with the screw 30a of FIGS. 8A and 8B, the lobes 174 of the pilot 170 would desirably be sized and contoured to have a slip fit with the spaces 68a in the head 40a of the screw 30a. The spaces 176 between the lobes 174 could be sized and contoured to form a slip fit with the lobes 66a of the screw 30a. Consequently, the portion 182 could have a hexalobe axial cross-section, similar to the hexalobe axial cross-section of the recess 50a.

The inner surface 189 would desirably be sized and contoured to engage with and/or form a provisional engagement and/or friction fit with the projection 110a on the screw 30a. More specifically, the inner surface 189 may have a corresponding polygonal cross-section which included a frustoconical shape that tapers inwardly in a direction extending from the axial end surface 168 towards the body 160. The axial cross-section and taper of the inner surface 189 could be such that the inner surface and projection 110a desirably form a friction fit with one another within the recess 190, which may include a series of corresponding flat inner surfaces and/or a curved or rounded inner surface(s), if desired. The inner surface 189 may be configured to allow the pilot 170 to abut the inner end surface 54a or the pilot may be spaced from the inner surface when the provisional engagement and/or friction fit is formed.

Figure 9A:
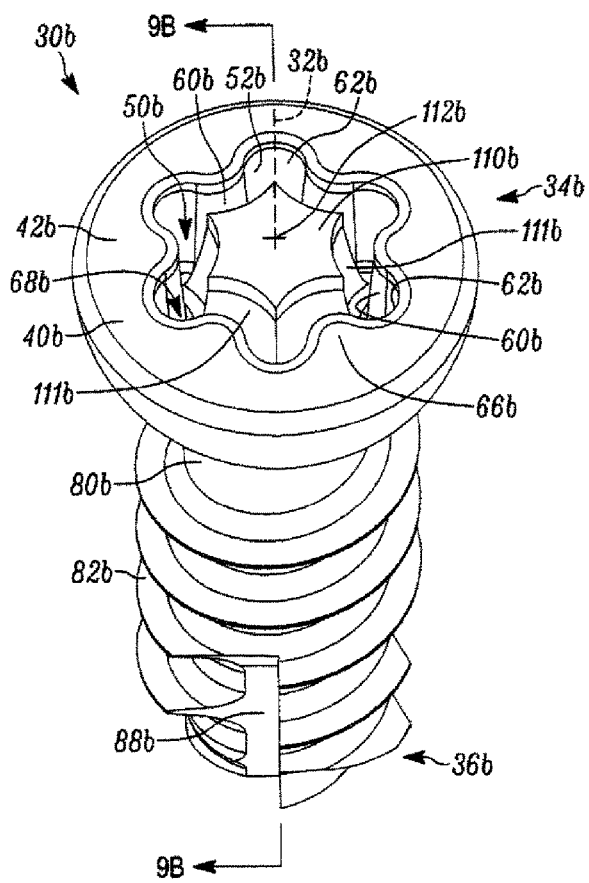
FIGS. 9A and 9B illustrate a fastener having another alternative configuration.
Figure 9B:
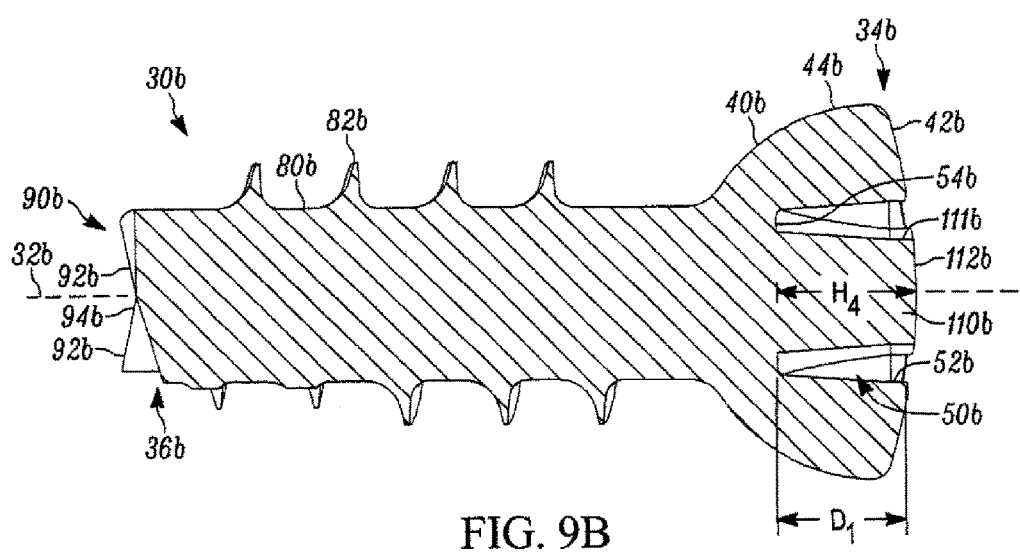

Referring to FIGS. 9A and 9B, another embodiment of the fastener could include a head 40b of the screw 30b including a projection 110b and a lobed inner surface 52b that defines the recess 50b. The projection 110b can have a polygonal axial cross-section with a plurality of concave sides 111b. In one example, the projection 110b can have the same number of sides 111b as the number of lobes 66b defined by the inner surface 52b. It will be appreciated, however, that the projection 110b may have more or fewer sides 111b than the number of lobes 66b. Each side 111b may be radially aligned with a corresponding first portion 60b or may be radially offset from the first portions (not shown).

The projection 110b desirably tapers in a radially inward direction relative to the axis 32b as the projection extends from the inner end surface 54b towards the axial end surface 42b. Each of the tapering sides 111b can be concave. The proximal extent 112b of the projection 110b can have the same radius of curvature as the axial end surface 42b. In the depicted embodiment, the projection 110b extends axially beyond the axial end surface 42b of the head 40b. In other words, the height $H_4$ of the projection 110b measured from the inner end surface 54b to the proximal extent 112b is greater than the depth $D_1$ of the recess 50b. In alternative embodiments, however, the height $H_4$ of the projection 110b may be equal to or less than the depth $D_1$ of the recess 50b (not shown).

Although not shown, the lobes 174 of a corresponding screwdriver 150 that can cooperate with the screw 30b would desirably be sized and contoured to have a slip fit with the spaces 68b in the head 40b of the screw 30b. The spaces 176 between the lobes 174 can be sized and contoured to form a slip fit with the lobes 66b of the screw 30b. Consequently, the portion 182 has a hexalobe axial cross-section. The inner surface 189 can be sized and contoured to form a provisional engagement and/or friction fit with the projection 110b on the screw 30b. More specifically, the inner surface 189 has a polygonal axial cross-section with convex sides (not shown). The inner surface 189 can taper inwardly in a direction extending from the axial end surface 168 towards the body 160. The axial cross-section and taper of the inner surface 189 is such that the inner surface and projection 110b form a provisional engagement and/or friction fit with one another within the recess 190. The inner surface 189 may be configured to allow the pilot 170 to contact and/or "bottom out" within the recess 50b or the pilot may be spaced from the inner end surface 54b when the friction fit is formed.

Figure 10A:
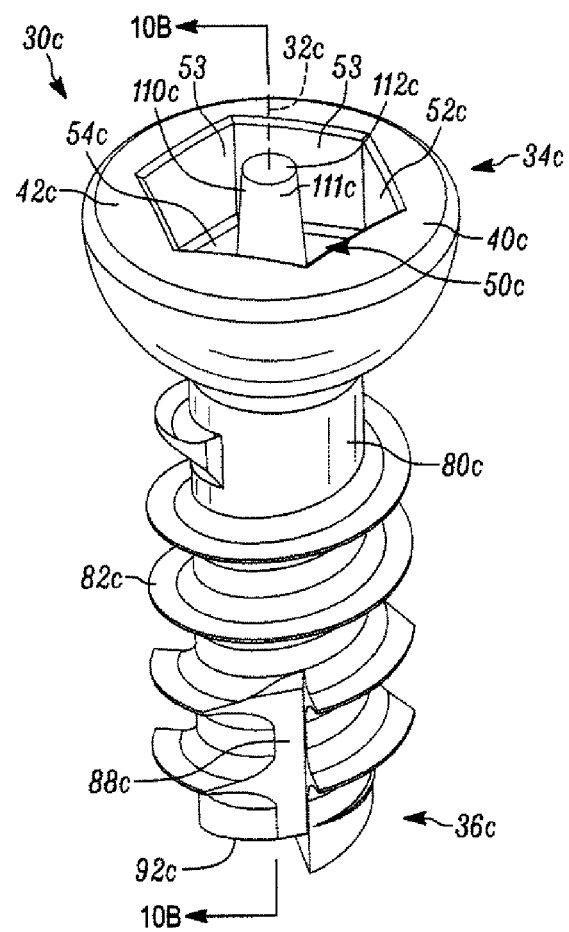
FIGS. 10A and 10B illustrate a fastener having another alternative configuration.
Figure 10B:
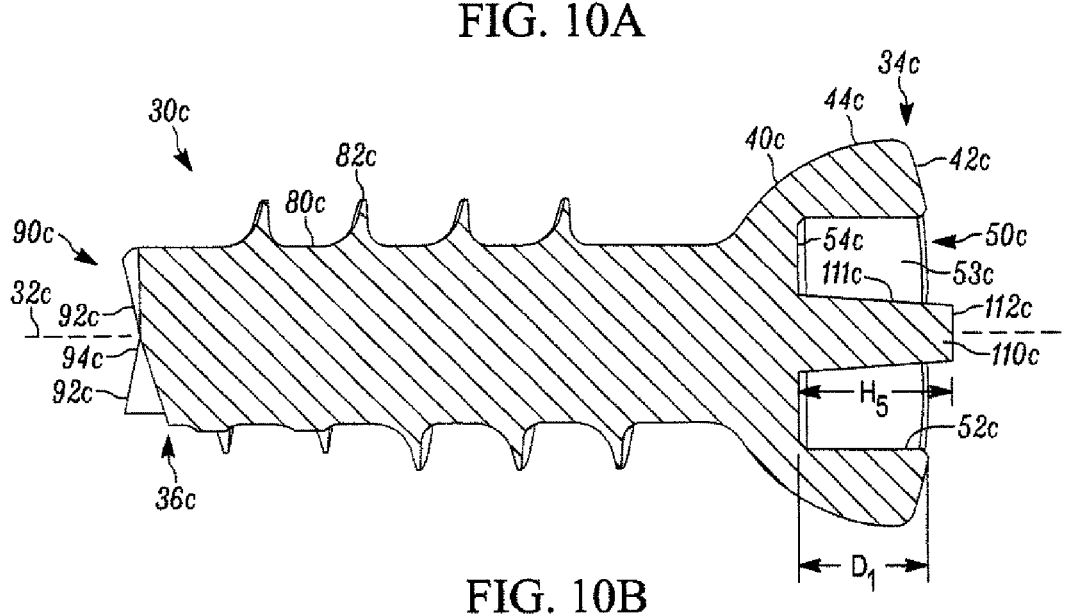

Referring to FIGS. 10A and 10B, another embodiment of the fastener could include an inner surface 52c of the screw 30c that has substantially planar surfaces 53, desirably forming a hexagonal shape about the axis 32c. Although six planar surfaces 53 are illustrated it will be appreciated that the inner surface 52c may include more or fewer planar surfaces defining any desired polygonal shape. The planar surfaces 53 extend parallel to the axis 32c but may alternatively taper inwards in a direction extending toward the inner end surface 54c (not shown).

In this embodiment, the projection 110c has a frustoconical shape, which can function particularly well to facilitate alignment and positioning of the driver within the recess. The projection 110c continuously tapers in a radially inward direction relative to the axis 32c as the projection extends from the inner end surface 54c towards the axial end surface 42c. The projection 110c extends axially beyond the axial end surface 42c of the head 40c—in other words, the height $H_5$ of the projection 110c measured from the inner end surface 54c to the proximal extent 112c is greater than the depth $D_1$ of the recess 50c. This arrangement can be particularly useful to a user of the fixation system, in that during "loading" of the fixation screw onto the driving tool, the projection 110c can be partially inserted into the opening 190 (with the projection tip desirably smaller than the opening and such insertion visually verifiable) and the screw rotated to align the recess with the lobes 174 of the driving tool, and then the screw can be fully seated onto the tool. Of course, in alternative embodiments the height $H_5$ of the projection 110c may be equal to or less than the largest depth $D_1$ of the recess 50c (not shown).

Although not shown, the lobes 174 of the screwdriver 150 that cooperate with the screw 30c can be sized and contoured to have a slip fit with the planar surfaces 53 in the head 40c of the screw 30c. Consequently, the portion 182 has a hexagonal axial cross-section similar to the hexagonal axial cross-section of the recess 50c. The inner surface 189 can be sized and contoured to form a provisional engagement and/or friction fit with the projection 110c on the screw 30c. More specifically, the inner surface 189 has a shape that cooperates with the frustoconical shape of the projection, which may include a corresponding frustoconical shape for the inner surface that tapers inwardly in a direction extending from the axial end surface 168 towards the body 160. The axial cross-section and taper of the inner surface 189 is such that the inner surface and projection 110c form a provisional engagement and/or friction fit with one another within the recess 190. The inner surface 189 may be configured to allow the pilot 170 to bottom out within the recess 50c or the pilot may be spaced from the inner end surface 54c when the friction fit is formed.

Figure 11A:
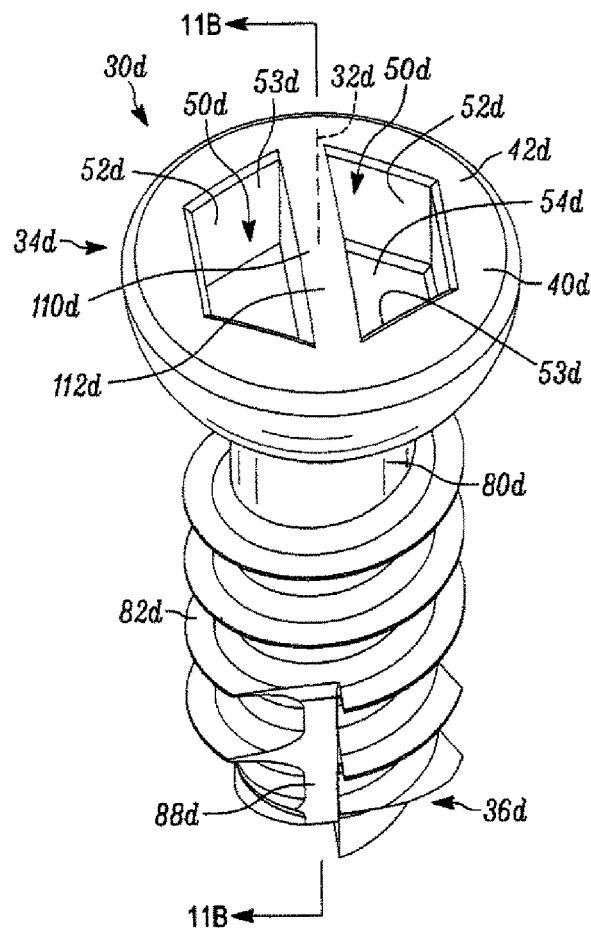
FIGS. 11A and 11B illustrate a fastener having another alternative configuration.
Figure 11B:
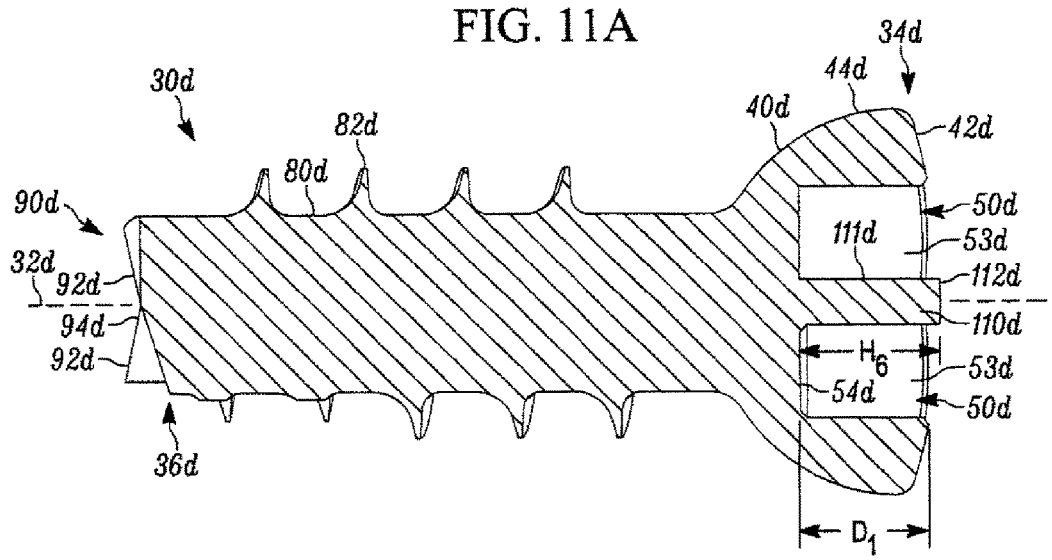

Referring to FIGS. 11A and 11B, another embodiment of the fastener could include an inner surface 52d and projection 110d of the screw 30d that desirably cooperate to form a plurality of polygonal recesses 50d in the head 40d of the screw 30d. More specifically, six planar surfaces 53d of the inner surface 52d can cooperate with the projection 110d and the inner end surface 54d to form a pair of trapezoidal recesses 50d in the head 40d of the screw 30d. It will be appreciated, however, that the head 40d may include any number of projections 110d in order to form a desired number of recesses 50d.

In this embodiment, the projection 110d desirably extends longitudinally along the axis 32d and radially between opposing sides of the inner surface 52d. The projection 110d extends axially beyond the axial end surface 42d of the head 40d. In other words, the height $H_6$ of the projection 110d measured from the inner end surface 54d to the proximal extent 112d is greater than the depth $D_1$ of the recess 50d. The height $H_6$ of the projection 110d may, however, be equal to or less than the depth $D_1$ of the recess 50d (not shown).

Although not shown, it will be appreciated that a pilot 170 for a screwdriver 150 configured to engage with and/or form a provisional engagement and/or friction fit with the screw 30d can include a bifurcated or multi-section tip configuration to accommodate one or more of each discrete recess 50d. In other words, such a pilot 170 could desirably have multiple, discrete portions corresponding in shape(s) and number with the shape(s) and number of recesses 50d in the screw 30d. The pilot 170 in this embodiment could form a provisional engagement and/or friction fit with the projection 110d and a slip fit with the planar surfaces 53d of the recess 50d.

Figure 12A:
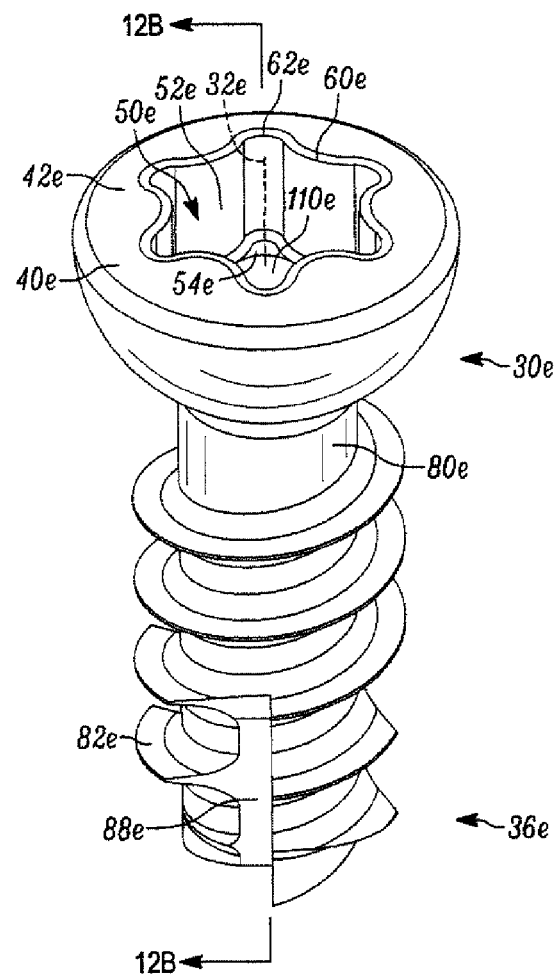
FIGS. 12A and 12B illustrate a fastener having another alternative configuration.
Figure 12B:
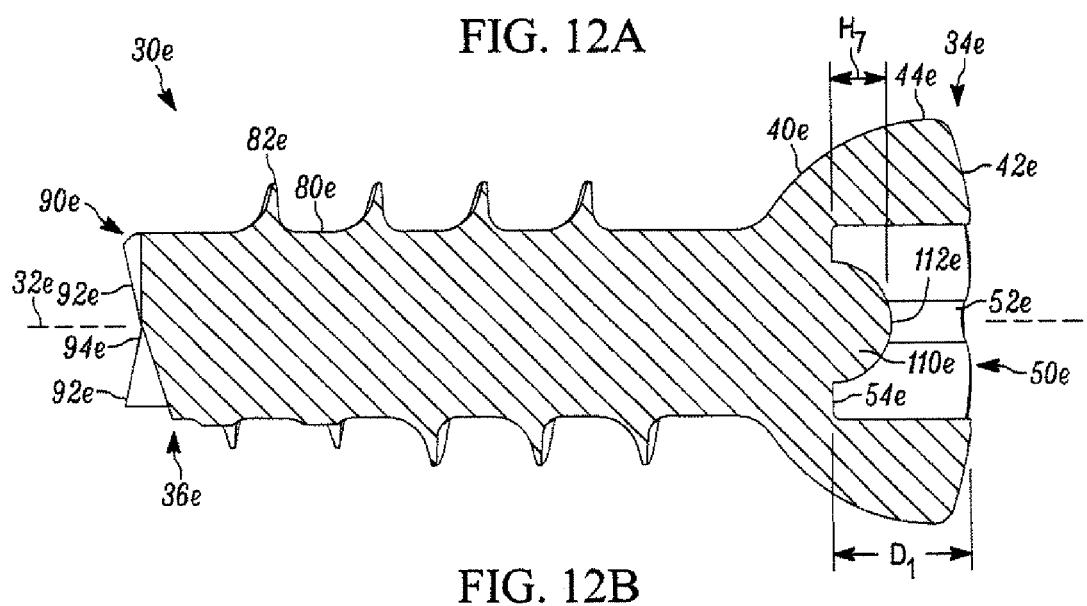

Referring to FIGS. 12A and 12B, another embodiment of the fastener could include a head 40e of the screw 30e incorporating a projection 110e and a lobed inner surface 52e that defines the recess 50e. The projection 110e in this embodiment has a domed or hemispherical shape. The projection 110e extends from the axial end surface 54e to a proximal extent 112e along the axis 32e. The projection 110e has a height $H_7$ measured from the axial end surface 54e to the proximal extent 112e. The height $H_7$ is less than the depth $D_1$ of the recess 50e. The height $H_7$ of the projection 110e may, however, be equal to or greater than the depth $D_1$ of the recess 50e (not shown).

Although not shown, the lobes 174 of the screwdriver 150 that could cooperate with the screw 30e would desirably be sized and contoured to have a slip fit with the spaces 68e in the head 40e of the screw 30e. The spaces 176 between the lobes 174 can be sized and contoured to form a slip fit with the lobes 66e of the screw 30e. Consequently, the portion 182 has a hexalobe axial cross-section that is similar to the hexalobe axial cross-section of recess 50e. The inner surface 189 can be sized and contoured to engage with and/or form a provisional engagement and/or friction fit with the projection 110e on the screw 30e. More specifically, the inner surface 189 can have a frustoconical shape (not shown). The inner surface 189 could taper inwardly in a direction extending from the axial end surface 168 towards the body 160. The axial cross-section and taper of the inner surface 189 is such that the inner surface and projection 110e form a provisional engagement and/or friction fit with one another within the recess 190. The inner surface 189 may be configured to allow the pilot 170 to bottom out within the recess 50e or the pilot may be spaced from the inner end surface 54e when the provisional engagement and/or friction fit is formed.

Referring to FIGS. 13A through 13D, another embodiment of the fastener could include a projection 110f having a circular axial cross-section and a generally frustoconical shape. It will be appreciated, however, that the projection 110f may have a variety of different axial cross-sections and/or shapes. The projection 110f can taper continuously in a radially inward direction relative to the axis 32f as the projection extends from the inner end surface 54f towards the axial end surface 42f. In the disclosed embodiment, the projection 110f extends axially beyond the axial end surface 42f of the head 40f—in other words, the height $H_8$ of the projection 110f measured from the inner end surface 54f to the proximal extent 112f is greater than the depth $D_1$ of the recess 50f. The height $H_8$ of the projection 110f may, however, be equal to or less than the depth $D_1$ of the recess 50f (not shown).

In this embodiment, a bore or passage 113f is formed in the projection 110f. The passage 113f desirably extends from the proximal extent 112f towards the second end 36f of the screw 30f. In one example, the passage 113f extends through the entire screw 30f, creating a fully cannulated screw (i.e., which may have particularly utility in wire-guided medical surgical procedures or similar applications). Alternatively, the passage 113f may extend through a portion or all of the projection 110f or terminate at a position along the shaft 80f (not shown). The passage 113f desirably has a circular axial cross-section and a cylindrical shape, although various alternative shapes may be incorporated, if desired. The passage 113f is depicted centered on the axis 32f.

Figure 13A:
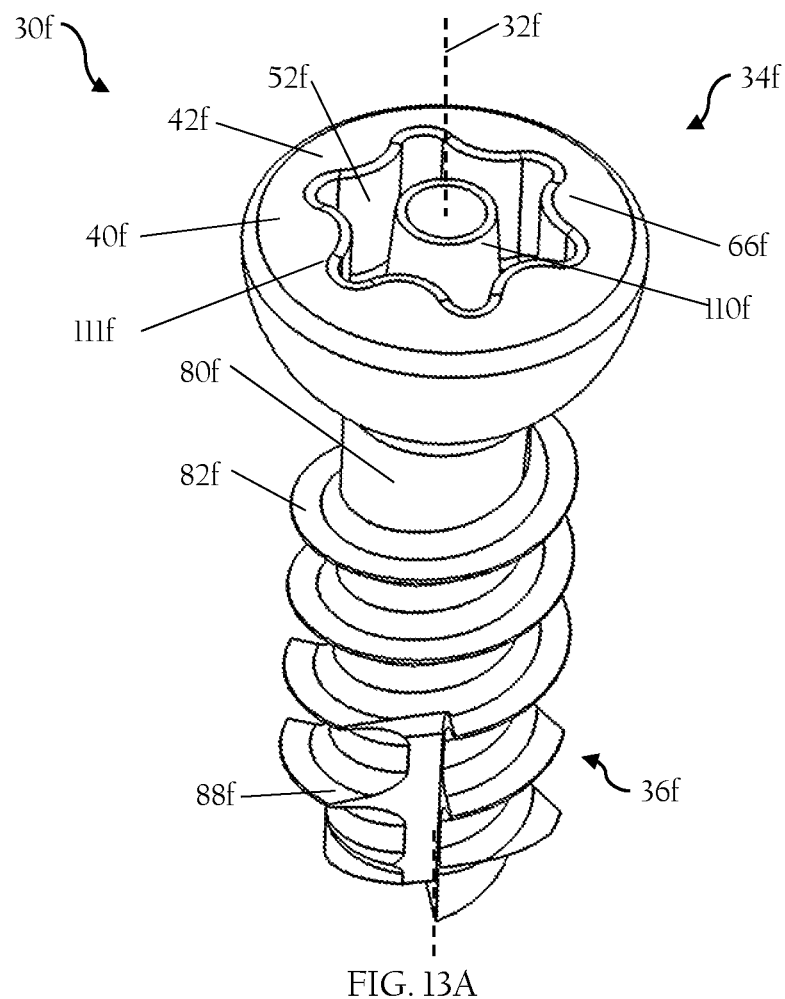
FIGS. 13A through 13D illustrate various view of a fastener having another alternative configuration.
Figure 13B:
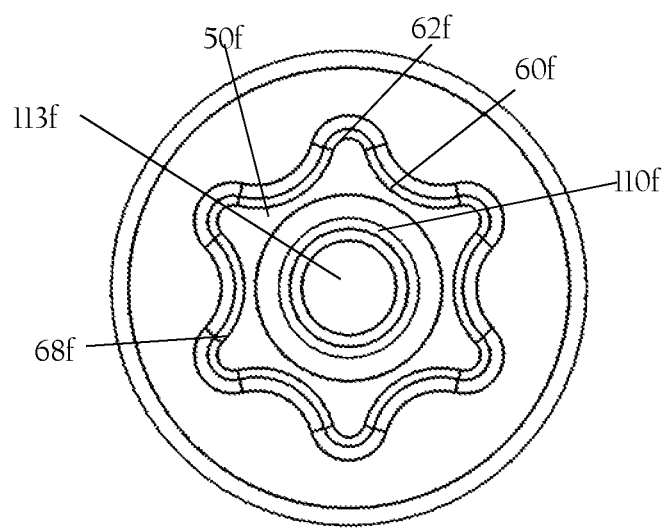
Figure 13C:
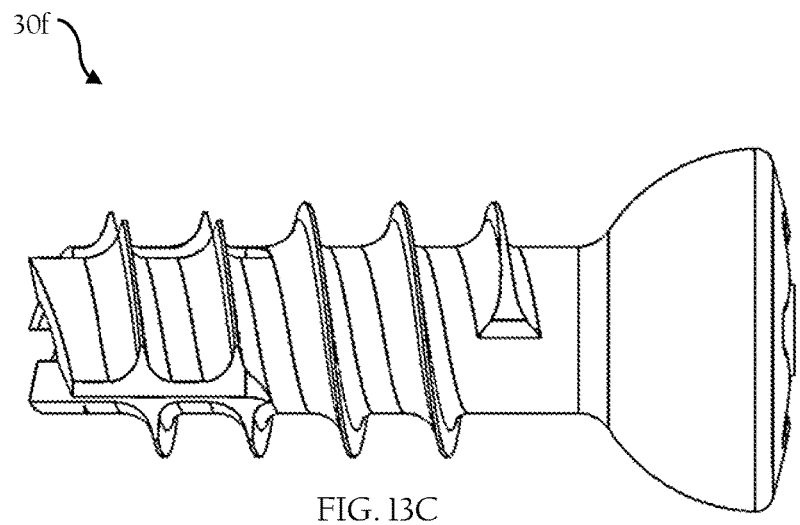
Figure 13D:
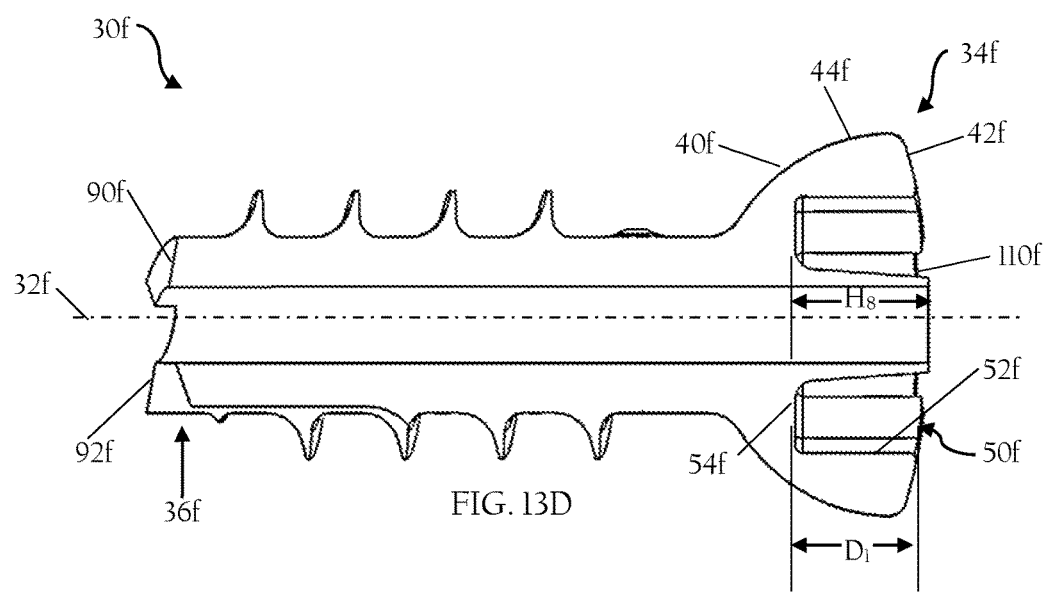

Although not shown, it should be appreciated that a fixation tool, such as a screwdriver 150, for use with the fastener or screw 30f of FIGS. 13A and 13B could be configured to cooperate with the screw 30f in a similar manner to how the screwdriver 150 cooperates with the screw 30 of FIGS. 2-4. In particular, with the screw 30f of FIGS. 13A and 13B, the lobes 174 of the pilot 170 could be sized and contoured to engage with and/or have a slip fit with the spaces 68f in the head 40f of the screw 30f. The spaces 176 between the lobes 174 would desirably be sized and contoured to form a slip fit with the lobes 66f of the screw 30f. Consequently, the portion 182 could have a hexalobe axial cross-section similar to the hexalobe axial cross-section of the recess 50f.

In this embodiment, the inner surface 189 of the fixation tool could be sized and contoured to engage with the projection 110f on the screw 30f (i.e., desirably forming a friction fit or other engagement feature). More specifically, the inner surface 189 may have a circular axial cross-section and a frustoconical shape that tapers inwardly in a direction extending from the axial end surface 168 towards the body 160. The axial cross-section and taper of the inner surface 189 could be such that the inner surface and projection 110f engage with and/or form a provisional engagement and/or friction fit with one another within the recess 190. The inner surface 189 may be configured to allow the pilot 170 to abut the inner end surface 54f or the pilot may be spaced from the inner surface when the provisional engagement and/or friction fit is formed.

If desired, the driving tool may similarly incorporate a longitudinally-extending opening or cannulation (not shown) which could be used to follow a guide wire with the fastener and attached tool.

In another alternative embodiment, a projection (not shown) may extend from the axial end surface 191 of the fixation tool, with the projection sized and/or shaped to fit into and/or cooperate with the passage 113f in the screw 30f to assist the user in aligning the screwdriver 150 and screw 30f along the axes 32f, 152. To this end, this projection may have a circular axial cross-section and may taper inwardly in a direction extending distally along the axis 152, if desired.

Referring to FIGS. 14A through 14E, another embodiment of a fastener could include a projection 110g having a circular axial cross-section and a generally cylindrical shape. It will be appreciated, however, that the projection 110g may have a variety of different axial cross-sections, heights and/or shapes. In this embodiment, the projection 110g desirably extends axially beyond the axial end surface 42g of the head 40g. In other words, the height $H_9$ of the projection 110g measured from the inner end surface 54g to the proximal extent 112g is greater than the depth $D_1$ of the recess 50g. The height $H_9$ of the projection 110g may, however, be equal to or less than the depth $D_1$ of the recess 50g (not shown).

A bore or passage 113g can be formed in the projection 110g. In this embodiment, the passage 113g comprises a transverse slot that has a rectangular axial cross-section and extends from the proximal extent 112g towards the second end 36g of the screw 30g. The passage 113g can taper inwardly in a direction extending towards the second end 36g of the screw 30g. The passage 113g terminates at an inner end surface 115g within the projection 110g, although the inner end surface may alternatively be positioned within the body 80g (not shown). The inner end surface 115g may therefore be substantially coplanar with the inner end surface 54g or spaced axially from the inner end surface in the proximal or distal direction along the axis 32g. As depicted, the passage 113g extends radially from the axis 32g through the entire projection 110g and divides the proximal end of the projection into two distinct portions. If compressed together, the two distinct portions may create a force directed radially outward when engaged with the pilot, desirably creating a higher provisional engagement force. It will be appreciated that the passage 113g may be configured shallower within the recess, may create thicker and/or thinner projections and/or may be configured to divide the projection 110g into more or fewer distinct portions (i.e., using multiple slots, etc.). Desirably, the passage 113g will be centered on the axis 32g, which desirably allows the portions of the projection 110g to radially deflect relative to the axis and to one another.

Figure 14A:
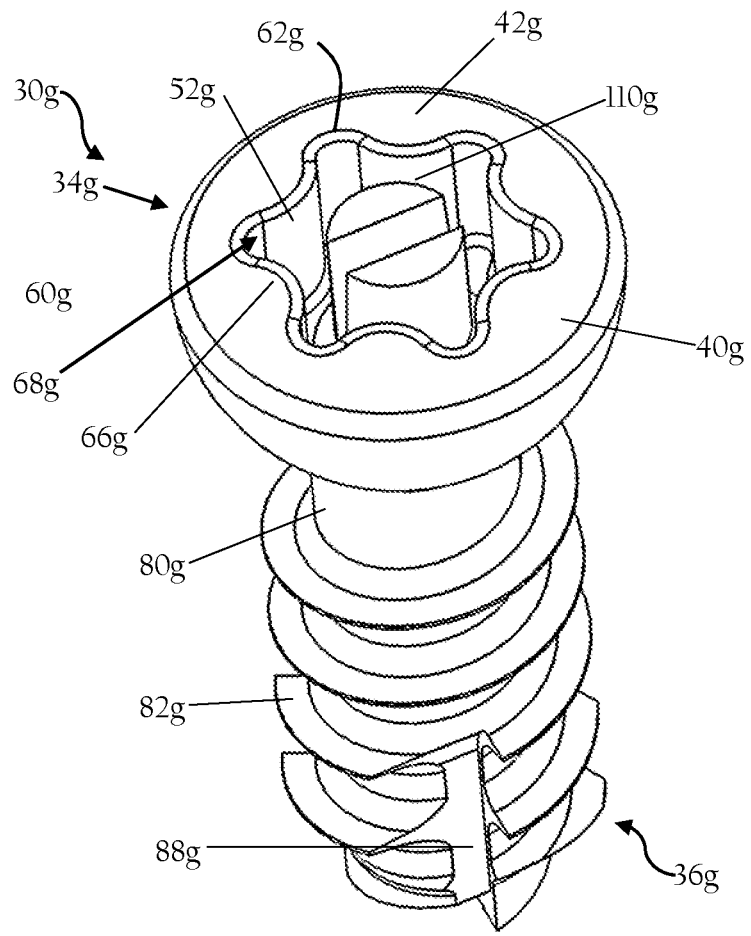
FIGS. 14A through 14E illustrate various views of a fastener having another alternative configuration.
Figure 14B:
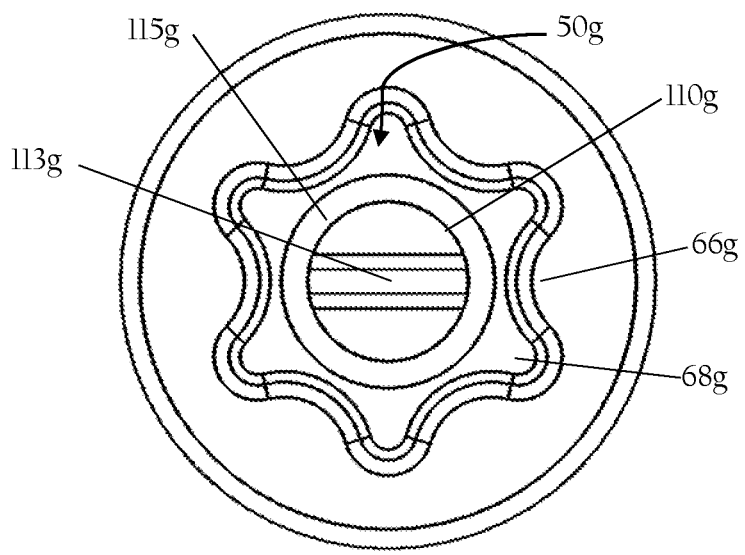
Figure 14C:
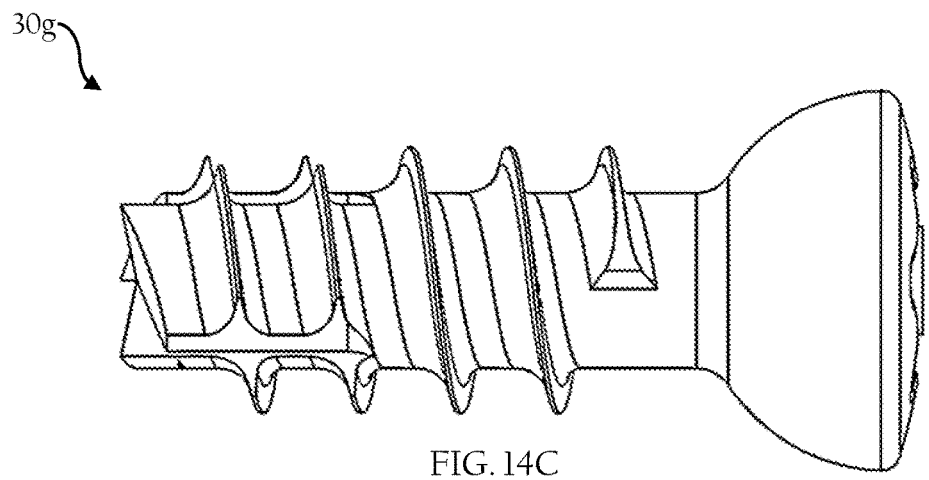
Figure 14D:
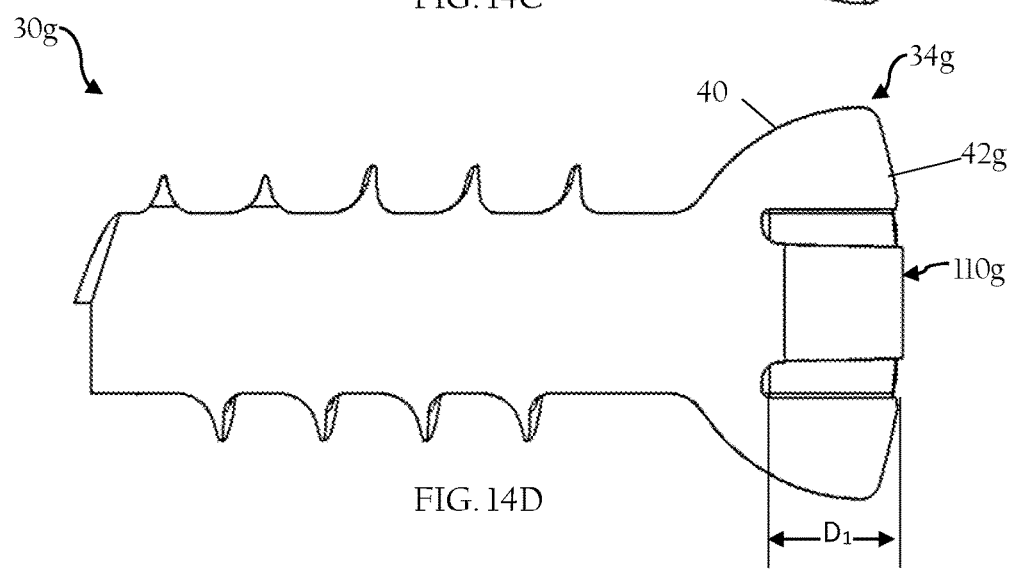
Figure 14E:
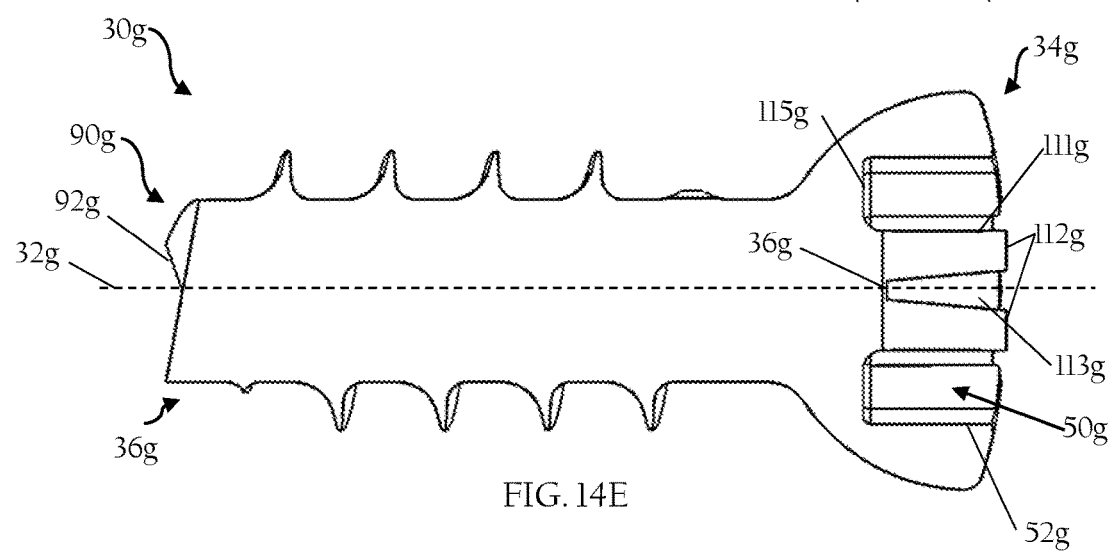

Although not shown, it will be appreciated that an appropriate driving tool or screwdriver 150 for use with the screw 30g of FIGS. 14A and 14B could be configured to cooperate with the screw 30g in a similar manner to how the screwdriver 150 cooperates with the screw 30 of FIGS. 2-4. In particular, with the screw 30g of FIGS. 14A and 14B, the lobes 174 of the pilot 170 are sized and contoured to have a slip fit with the spaces 68g in the head 40g of the screw 30g. The spaces 176 between the lobes 174 are sized and contoured to form a slip fit with the lobes 66g of the screw 30g. Consequently, the portion 182 has a hexalobe axial cross-section similar to the hexalobe axial cross-section of the recess 50g.

The inner surface 189 of the driving tool can be sized and contoured to engage with and/or form a friction fit with the projection 110g on the screw 30g. More specifically, the inner surface 189 may have a circular axial cross-section and may incorporate a generally cylindrical and/or frustoconical shape (i.e., including a frustoconical shape that tapers inwardly in a direction extending from the axial end surface 168 towards the body 160). The axial cross-section and optional taper of the inner surface 189 are such that the inner surface and projection 110g will desirably provisionally engage with and/or form a friction fit with one another within the recess 190. For example, the inner surface 189 may be sized to deflect the portions of the projection 110g inward towards the axis 32g such that the resistance of the projection portions to the deflection causes and/or enhances the provisional engagement and/or friction fit between the projection and the inner surface. The inner surface 189 may be configured to allow the pilot 170 to abut the inner end surface 54g or the pilot may be spaced from the inner surface when the provisional engagement and/or friction fit is formed.

In various alternative embodiments, a projection or other feature (not shown) may be disposed within the opening 190, extending from the axial end surface 191, and be sized and shaped for cooperating with the passage 113g in the screw 30g. If desired, the projection could engage with the passage 113g and potentially help align the screwdriver 150 and screw 30g along the axes 32g, 152. To this end, this projection may have a rectangular axial cross-section and may taper inwardly in a direction extending distally along the axis 152. In other embodiments, the projection might selectively extend into the passage 113g and desirably interfere with deflection or other movement of the projections, and in some embodiments might form a "locking feature" which selective locks and/or unlocks the provisional engagement feature between the screw and the driving tool.

Referring to FIGS. 15A-15D, another embodiment of a fastener could include a head 40h incorporating a series of radially extending passages 117h, which could provisionally engage with and/or provide a provisional engagement and/or friction fit with the screwdriver 150. Each passage 117h could extend radially through one of the concave portions 62h from the inner surface 52h to the rounded surface 44h. It will be understood that any number of passages 117h may be provided through any number of concave portions 62h.

In this embodiment, each passage 117h can also extends axially from the end surface 42h of the head 40h towards the inner surface 54h, terminating at an inner end surface 118h and dividing the head into six distinct portions. It will be appreciated that the passages 117h may be alternatively configured to divide the head 40h into more or fewer distinct portions. If desired, the passages 117h may extend lesser and/or greater depths within the head 40h to allow portions of the head to deflect relative to each other.

Each disclosed passage 117h can have a substantially rectangular axial cross-section that tapers inwardly in a direction extending from the end surface 42h towards the inner surface 118h. The passages 117h can have a depth or height $H_{10}$ measured from the inner end surface 118h to the end surface 42h that is less than the depth $D_1$ of the recess 50h. The height $H_{10}$ of the passages 117h may, however, be equal to or greater than the depth $D_1$ of the recess 50h such that the concave portions 62h are substantially or entirely omitted. The passages 117h are shown symmetrically arranged about the axis 32h, but may alternatively be asymmetrically arranged about the axis (not shown). The passages 117h are shown identical to one another, but may alternatively be different from one another (not shown).

Figure 15A:
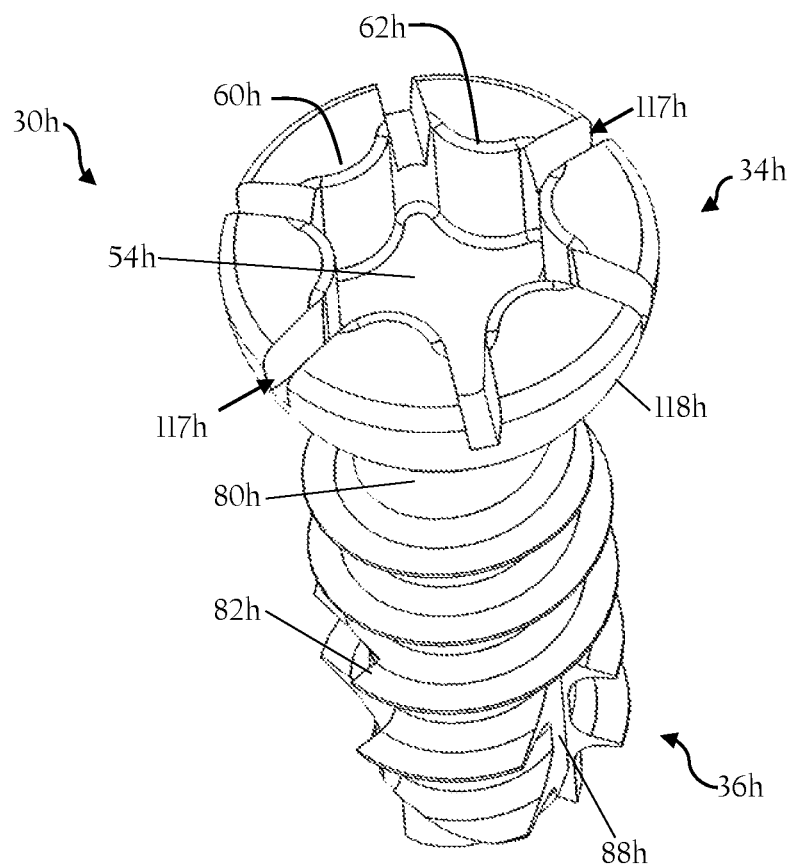
FIGS. 15A through 15D illustrate various views of a fastener having another alternative configuration.
Figure 15B:
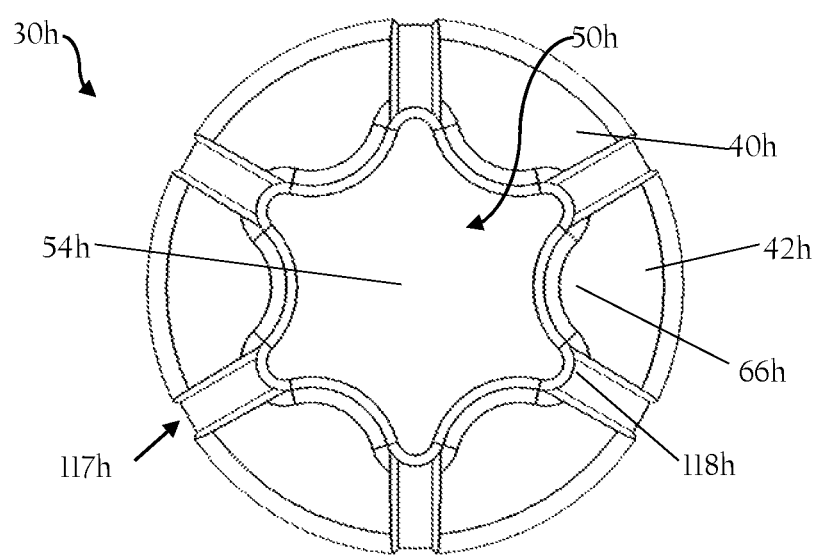
Figure 15C:
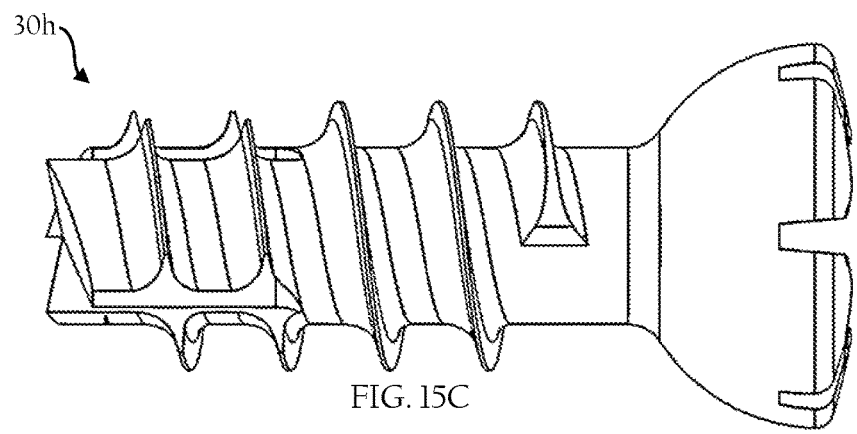
Figure 15D:
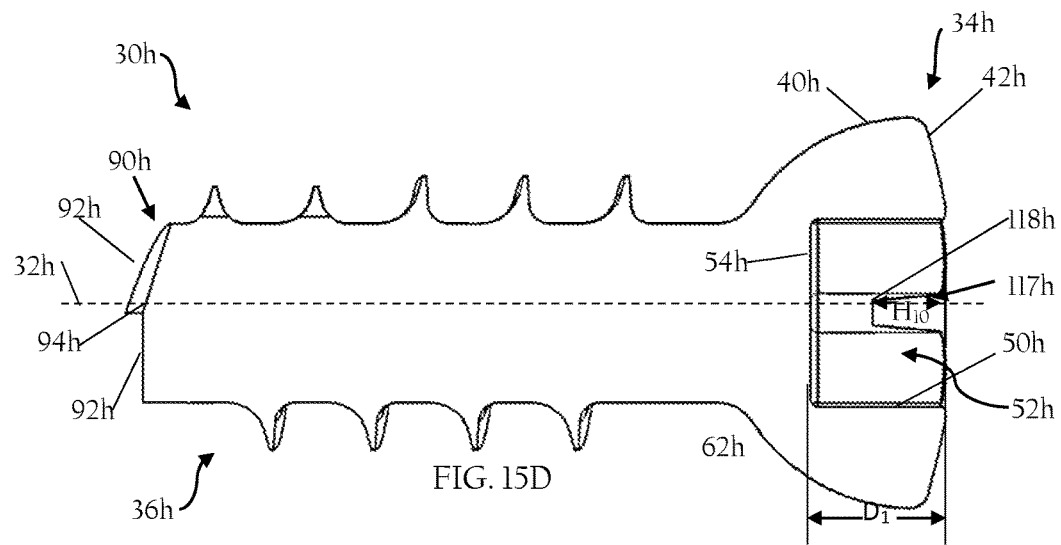

Although not shown, it will be appreciated that a driving tool or screwdriver 150 for use with the screw 30h of FIGS. 15A-15C could be configured to cooperate with the screw 30h in a similar manner to how the screwdriver 150 cooperates with the screw 30 of FIGS. 2-4. In particular, with the screw 30h of FIGS. 15A-15C, the spaces 176 between the lobes 174 can be sized and contoured to form a slip fit with the lobes 66h of the screw 30h. Consequently, the portion 182 can have a hexalobe axial cross-section similar to the hexalobe axial cross-section of the recess 50h. Alternatively, a standard or universal screwdriver or driving tool might be used to manipulate the screw (i.e., a flat-head or Philips-head screwdriver), if desired.

The pilot 170 of the driving tool will desirably include structure sized and contoured to engage with and/or form a provisional engagement and/or friction fit with the passages 117h on the screw 30h. More specifically, one or more projections may extend radially outward from the convex lobes 174 for mating with one or more of the passages 117h. Each projection on the lobes 174 can have a rectangular axial cross-section and frustoconical shape that tapers outwardly in a direction extending from the axial end surface 168 towards the body 160. The axial cross-section and taper of the projections on the lobes 174 can be formed such that one or more of the projections and passages 117h form a provisional engagement and/or friction fit with one another. If the portions of the head 40h are deflectable relative to one another, the resistance to deflection of the head portions by the inner surface 189 can further enhance the engagement and/or friction fit. The projections on the lobes 174 may be configured to allow the pilot 170 to abut the inner end surface 54h or the pilot may be spaced from the inner surface when the provisional engagement and/or friction fit is formed.

Referring to FIGS. 16A through 16D, another embodiment of a fastener could include a head 40i of the screw 30i is similar to the head 40b of the screw 30b of FIGS. 9A and 9B. The recess 50i and projection 110i of the screw 30i could be similar to the recess 50b and projection 110b of the screw 30b. The projection 110i can have a circular axial cross-section and a generally frustoconical shape and extends axially beyond the axial end surface 42i of the head 40i. In other words, the height $H_{11}$ of the projection 110i measured from the inner end surface 54i to the proximal extent 112i is greater than the depth $D_1$ of the recess 50i. The height $H_{11}$ of the projection 110i may, however, be equal to or less than the depth $D_1$ of the recess 50i (not shown).

In this embodiment, the projection 40i on the screw 30i further includes a bore or passage 113i extending from the proximal extent 112i towards the second end 36i of the screw 30i. In one example, the passage 113i extends through the entire screw 30i. Alternatively, the passage 113i may extend through a portion or all of the projection 110i or terminate at a position within the head and/or along the shaft 80i (not shown). The passage 113i can have a circular axial cross-section and a cylindrical shape, although various other shapes known in the art could be incorporated with varying levels of utility. As shown, the passage 113i can be centered on the axis 32i.

Figure 16A:
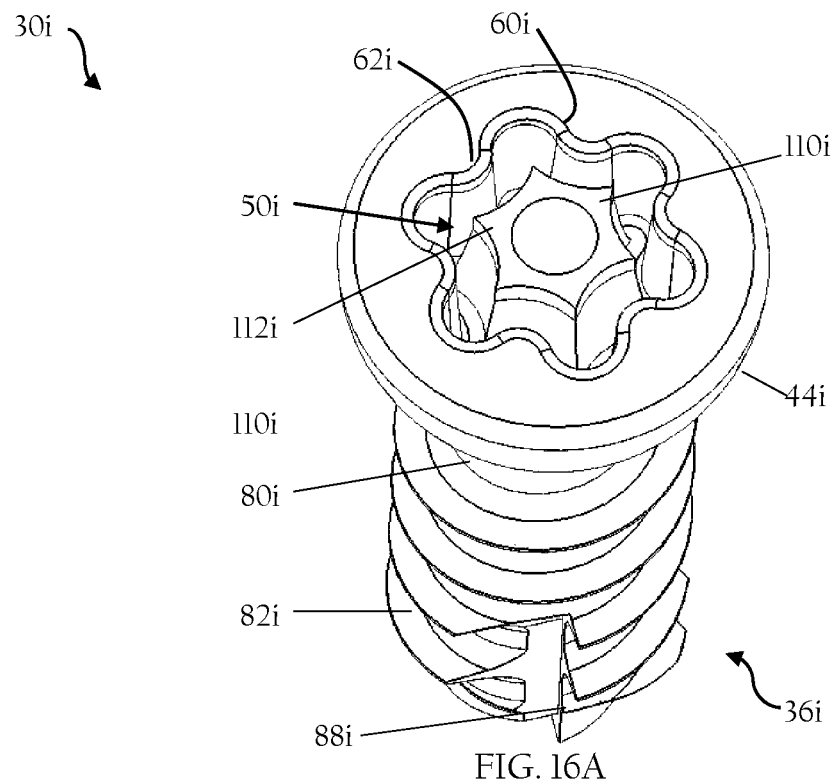
FIGS. 16A through 16D illustrate various views of a fastener having another alternative configuration.
Figure 16B:
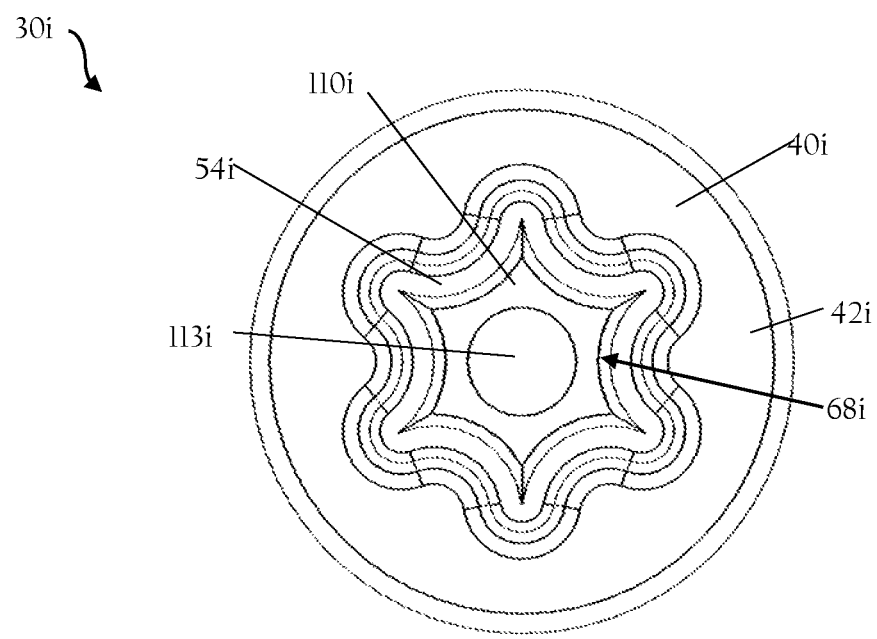
Figure 16C:
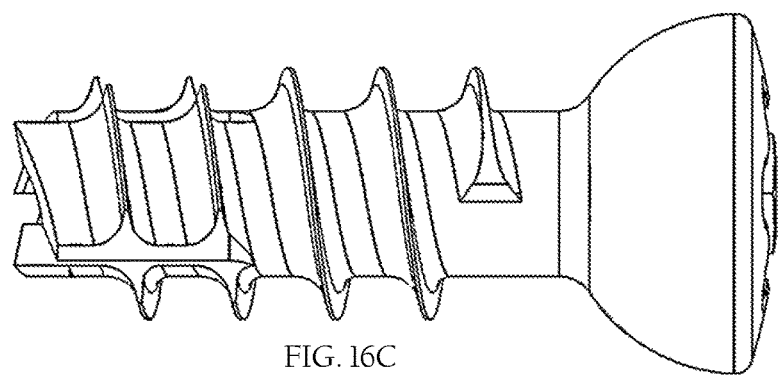
Figure 16D:
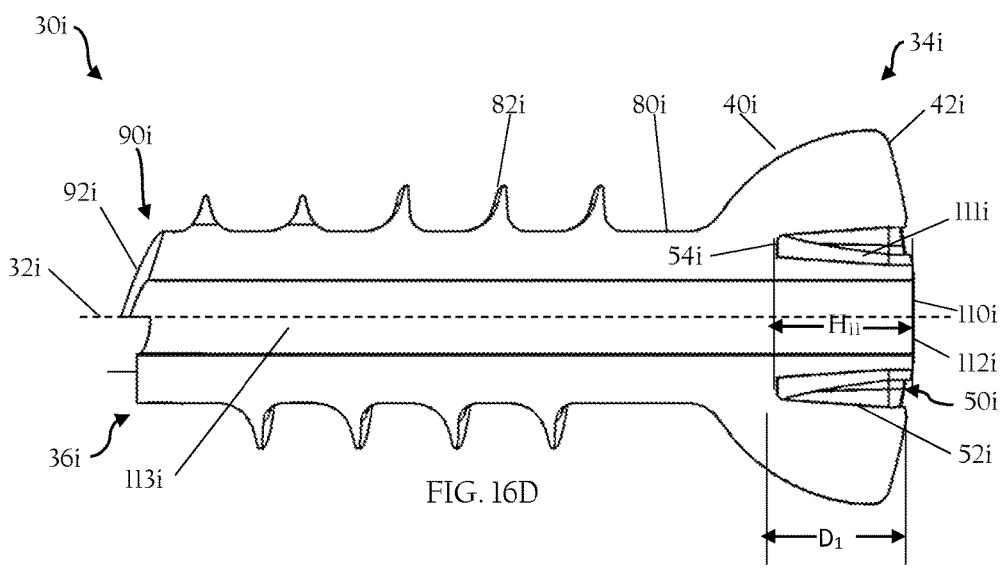

Although not shown, it will be appreciated that a driving tool or screwdriver 150 for use with the screw 30i of FIGS. 16A and 16B could be configured to cooperate with the screw 30i in a similar manner to how the screwdriver 150 cooperates with the screw 30 of FIGS. 2-4. The lobes 174 of the screwdriver 150 that cooperate with the screw 30i can be sized and contoured to engage with and/or have a slip fit with the spaces 68i in the head 40i of the screw 30i. The spaces 176 between the lobes 174 are sized and contoured to engage with and/or form a slip fit with the lobes 66i of the screw 30i. Consequently, the portion 182 can incorporate a hexalobular cross-section.

The inner surface 189 of the pilot 170 of a corresponding driving tool can be sized and contoured to engage with and/or form a friction fit with the projection 110i on the screw 30i. More specifically, the inner surface 189 can have a polygonal axial cross-section with convex sides (not shown). If desired, the inner surface 189 can taper inwardly in a direction extending from the axial end surface 168 towards the body 160. The axial cross-section and taper of the inner surface 189 can be such that the inner surface and projection 110i engage with and/or form a friction fit with one another within the recess 190. The inner surface 189 may be configured to allow the pilot 170 to bottom out within the recess 50i or the pilot may be spaced from the inner end surface 54i when the provisional engagement and/or friction fit is formed.

In various alternative embodiments, a projection may extend from the axial end surface 191 and be sized and shaped for cooperating with the passage 113i in the screw 30i to help align the screwdriver 150 and screw 30i along the axes 32i, 152. To this end, this projection may have a circular axial cross-section and a cylindrical shape.

Referring to FIGS. 17A through 17D, another embodiment of a fastener could include a head 40j of the screw 30j incorporating features similar to those of the head 40g of the screw 30g of FIGS. 14A and 14B. The recess 50j and projection 110j of the screw 30j can therefore be similar to the recess 50g and projection 110g of the screw 30g. In this embodiment, the projection 110j could extend longitudinally beyond the axial end surface 42j of the head 40j. In other words, the height $H_{12}$ of the projection 110j measured from the inner end surface 54j to the proximal extent 112j can be greater than the depth $D_1$ of the recess 50j. The height $H_{12}$ of the projection 110j may, however, be equal to or less than the depth $D_1$ of the recess 50j (not shown).

In this embodiment, the passage 113*j* in the projection 110*j* has an x-shaped axial cross-section and extends from the proximal extent 112*j* towards the second end 36*j* of the screw 30*j*. The passage 113*j* desirably extends substantially parallel to the axis 32*j* while extending towards the second end 36*j* of the screw 30*j*. The passage 113*j* desirably terminates at an inner end surface 115*j* within the projection 110*j*, although the inner end surface may alternatively be positioned in other locations with the head and/or within the body 80*j* (not shown). The inner end surface 115*j* may therefore be substantially coplanar with the inner end surface 54*j* or spaced axially from the inner end surface in the proximal or distal direction along the axis 32*j*.

The passage 113*j* can extend radially from the axis 32*j*, through the entire projection 110*j* (and/or some portions thereof) and divides the projection into four distinct portions. It will be appreciated that the passage 113*j* may be configured to divide the projection 110*j* into more or fewer distinct portions. If compressed together, the four distinct portions may create a force directed radially outward when engaged with the pilot creating a higher provisional engagement force. If desired, the passage 113*j* can desirably be centered on the axis 32*j* and the removal of the material (and amount of material removed) desirably allows the portions of the projection 110*j* to deflect to varying degrees relative to each other.

Figure 17A:
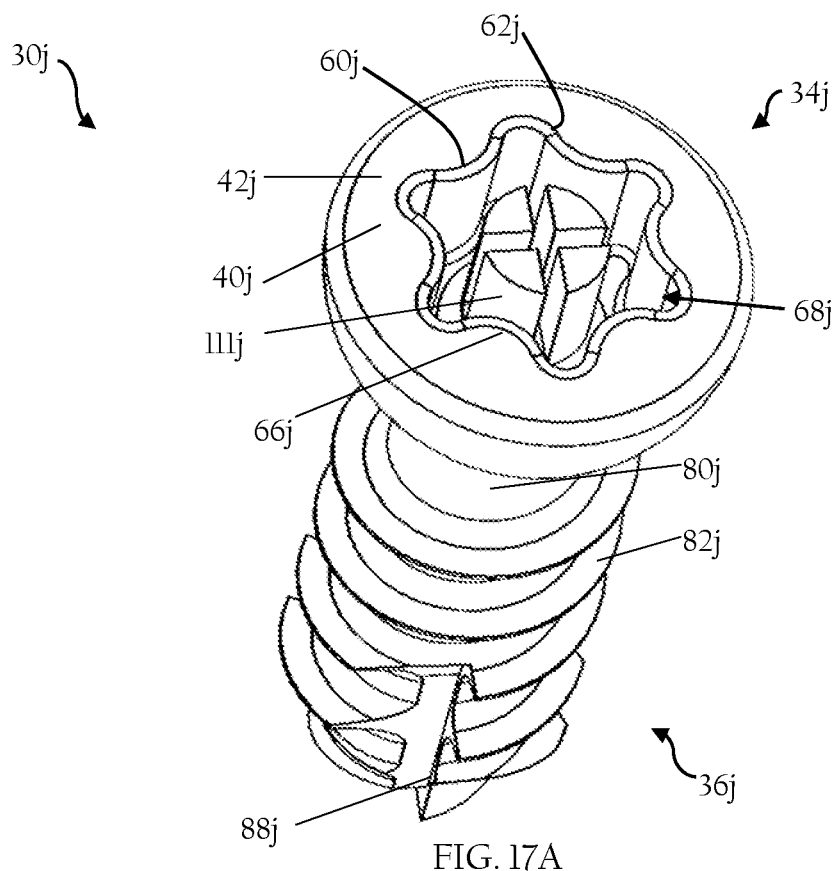
FIGS. 17A through 17D illustrate various views of a fastener having another alternative configuration.
Figure 17B:
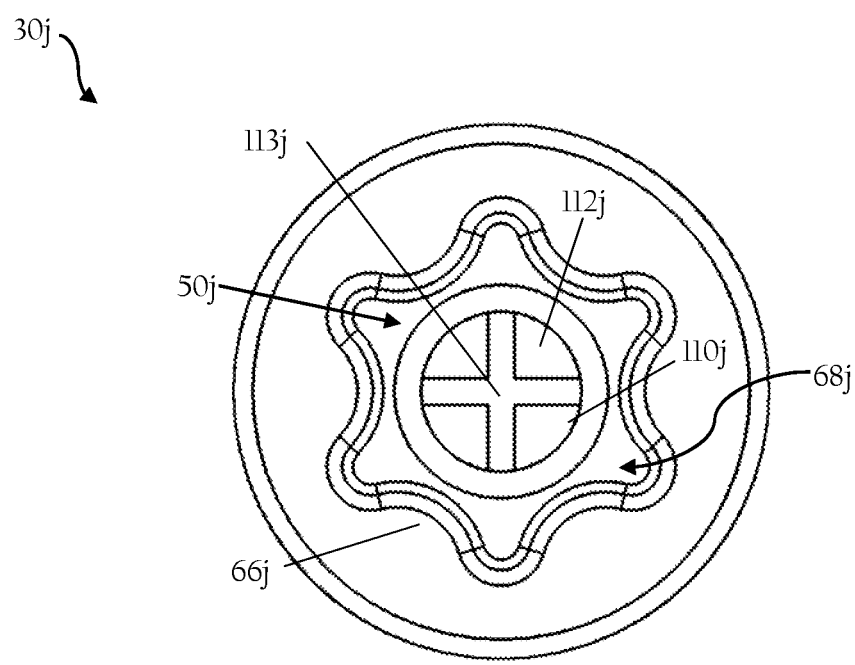
Figure 17C:
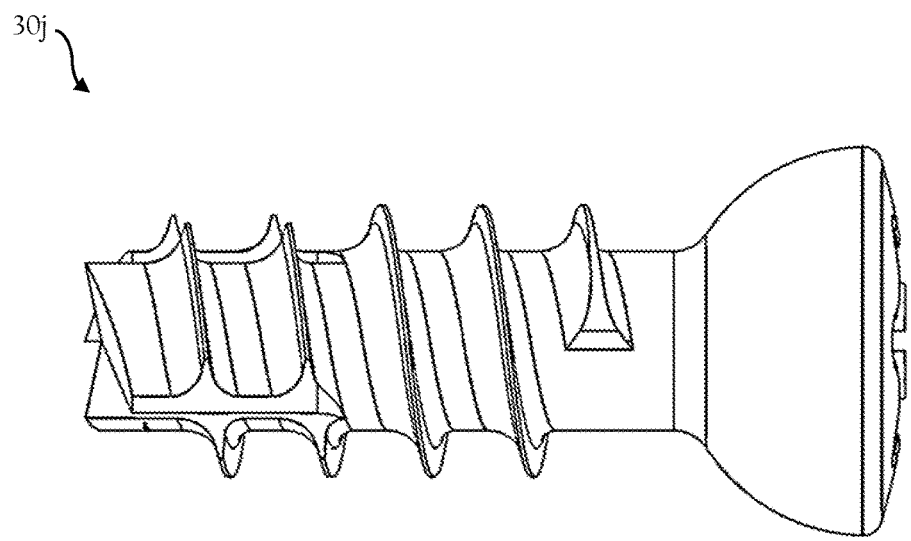
Figure 17D:
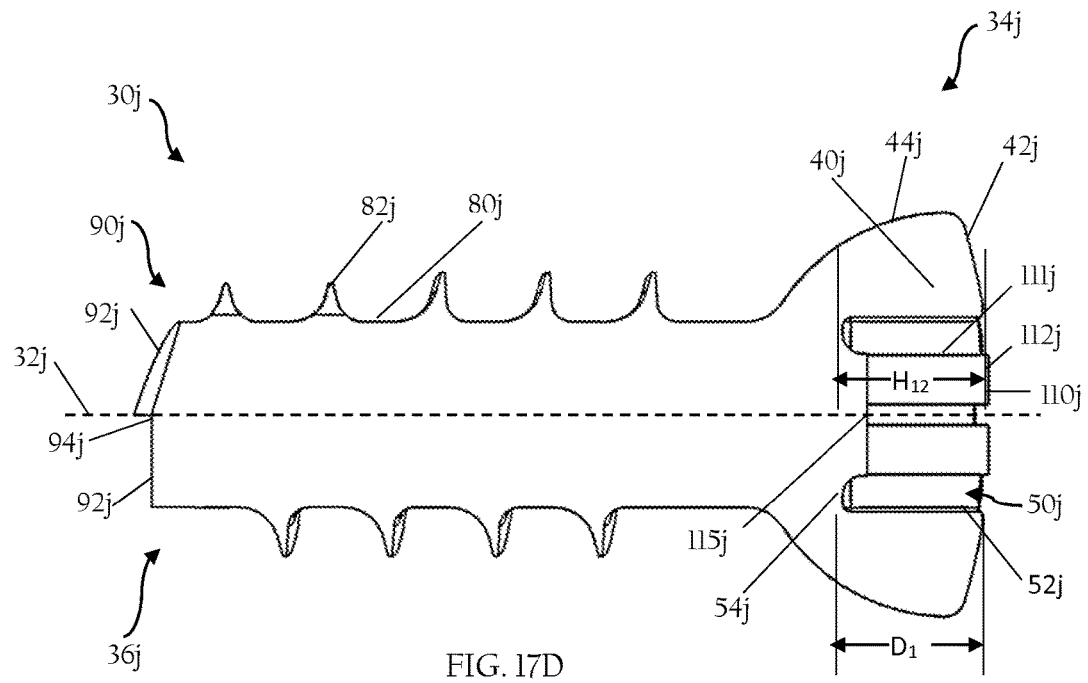

Although not shown, it will be appreciated that a driving tool or the screwdriver 150 for use with the screw 30*j* of FIGS. 17A and 17B could be configured to cooperate with the screw 30*j* in a similar manner to how the screwdriver 150 cooperates with the screw 30 of FIGS. 2-4. In particular, with the screw 30*j* of FIGS. 17A and 17B, the lobes 174 of the pilot 170 can be sized and contoured to have a slip fit with the spaces 68*j* in the head 40*j* of the screw 30*j*. The spaces 176 between the lobes 174 can be sized and contoured to form a slip fit with the lobes 66*j* of the screw 30*j*. Consequently, the portion 182 can have a hexalobe axial cross-section similar to the hexalobe axial cross-section of the recess 50*j*.

In a corresponding driving tool or screwdriver, the inner surface 189 can be sized and contoured to engage with and/or form a provisional engagement and/or friction fit with the projection 110*j* on the screw 30*j*. More specifically, the inner surface 189 might have a circular axial cross-section and/or a cylindrical or frustoconical shape (i.e., that tapers inwardly in a direction extending from the axial end surface 168 towards the body 160). The axial cross-section and inner surface 189 can be sized and configured such that the inner surface and projection 110*j* desirably provisionally engage with each other (i.e., optionally including a friction fit with one another) within the recess 190. For example, the inner surface 189 of the opening 190 might be sized slightly smaller than the outer diameter of the projection, such that it deflects the portions of the projection 110*j* inward towards the axis 32*j*, desirably so that the resistance of the projection portions to the deflection can physically engage the components and/or enhance any provisional engagement and/or friction fit between the projection and the inner surface. The inner surface 189 may be configured to allow the pilot 170 to abut the inner end surface 54*j* or the pilot may be spaced from the inner surface when the provisional engagement and/or friction fit is formed.

If desired, a projection may extend from the axial end surface 191 and be sized and shaped for cooperating with the passage 113*j* in the screw 30*j* to help align the screwdriver 150 and screw 30*j* along the axes 32*j*, 152. To this end, this projection may have an x-shaped axial cross-section and be centered on the axis 152. In other embodiments, the projection might selectively extend into the passage 113*j* and desirably interfere with deflection or other movement of the projections, and in some embodiments might form a "locking feature" which selective locks and/or unlocks the provisional engagement feature between the screw and the driving tool.

Referring to FIGS. 18A through 18D, another embodiment of a fastener could incorporate a projection 110*k* having a first portion 121*k* with a cylindrical shape and a second portion 123*k* having a spherical shape. The first portion 121*k* can desirably extend along the axis 32*k*, away from the inner end surface 54*k*. The second portion 123*k* can extend along the axis 32*k* from the first portion 121*k*, away from the inner end surface 54*k*. The largest axial cross-section of the second portion 123*k* can be larger than the axial cross-section of the first portion 121*k*, thereby forming an undercut 124*k* between the first and second portions. The height $H_{13}$ of the projection 110*k* measured from the inner end surface 54*k* to the proximal extent can be less than the depth $D_1$ of the recess 50*k*. Alternatively, the height $H_{13}$ of the projection 110*k* may be equal to or greater than the depth $D_1$ of the recess 50*k* (not shown).

In this embodiment, the passage 113*k* in the projection 110*k* on the screw 30*k* can have an x-shaped axial cross-section, which extends from the proximal extent towards the second end 36*k* of the screw 30*k*. The passage 113*k* extends substantially parallel to the axis 32*k* while extending towards the second end 36*k* of the screw 30*k*. The passage 113*k* can terminate at an inner end surface 115*k* within the projection 110*k*, although the inner end surface may alternatively be positioned within the body 80*k* (not shown). The inner end surface 115*k* may therefore be substantially coplanar with the inner end surface 54*k* or spaced axially from the inner end surface in the proximal or distal direction along the axis 32*k*.

As shown, the passage 113*k* extends the entire length of the projection 110*k*. The passage 113*k* extends radially from the axis 32*k* through the entire projection 110*k* and desirably divides the projection into some number of distinct portions, which in this embodiment is four distinct portions. It will be appreciated that the passage 113*k* may be configured to divide the projection 110*k* into more or fewer distinct portions. If desired, the passage 113*k* can be centered on the axis 32*k* or can be off-centered. The passage desirably allows the portions of the projection 110*k* to radially deflect relative to the axis and/or one another, as well as create a force directed radially outward while the projections are compressed during their engagement with the pilot, potentially creating a higher provisional engagement force, if desired. Furthermore, the distinct portions in combination with the projection undercut 124*k* can significantly increases the provisional engagement force, if desired. Such projection undercut 124*k* may also provide an audible or tactile feedback, such as a click that confirms that the provisional engagement has occurred.

Figure 18A:
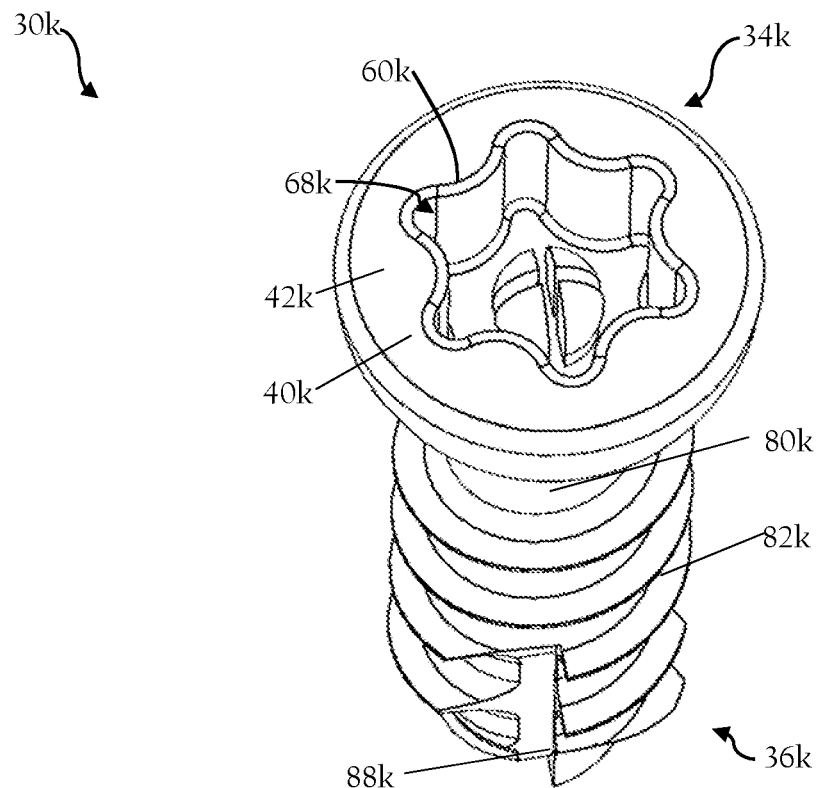
FIGS. 18A through 18D illustrate various views of a fastener having another alternative configuration.
Figure 18B:
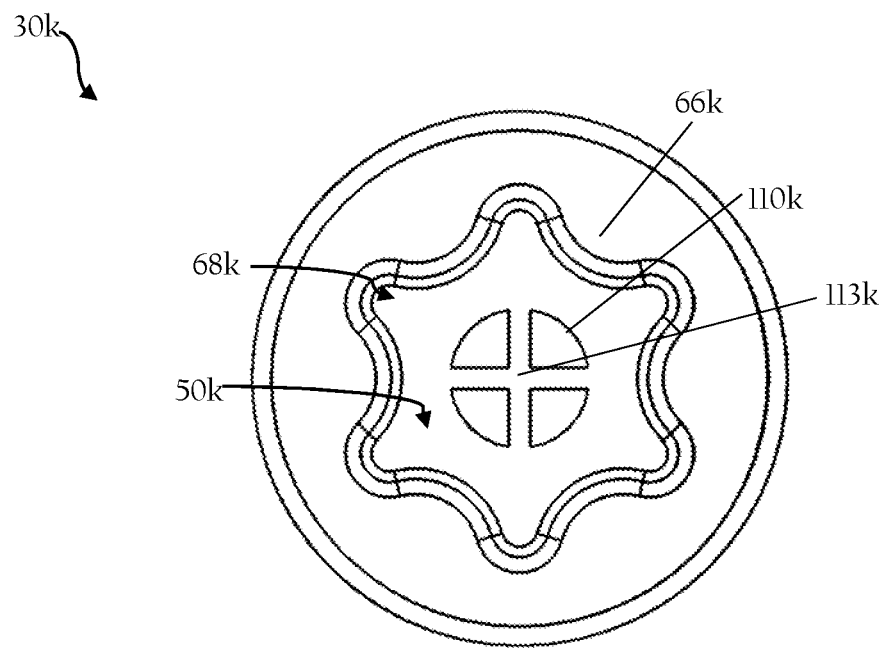
Figure 18C:
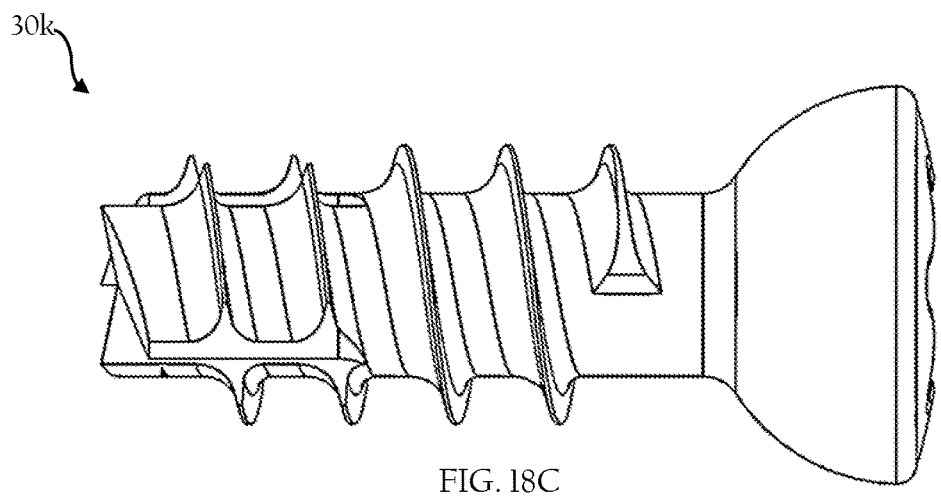
Figure 18D:
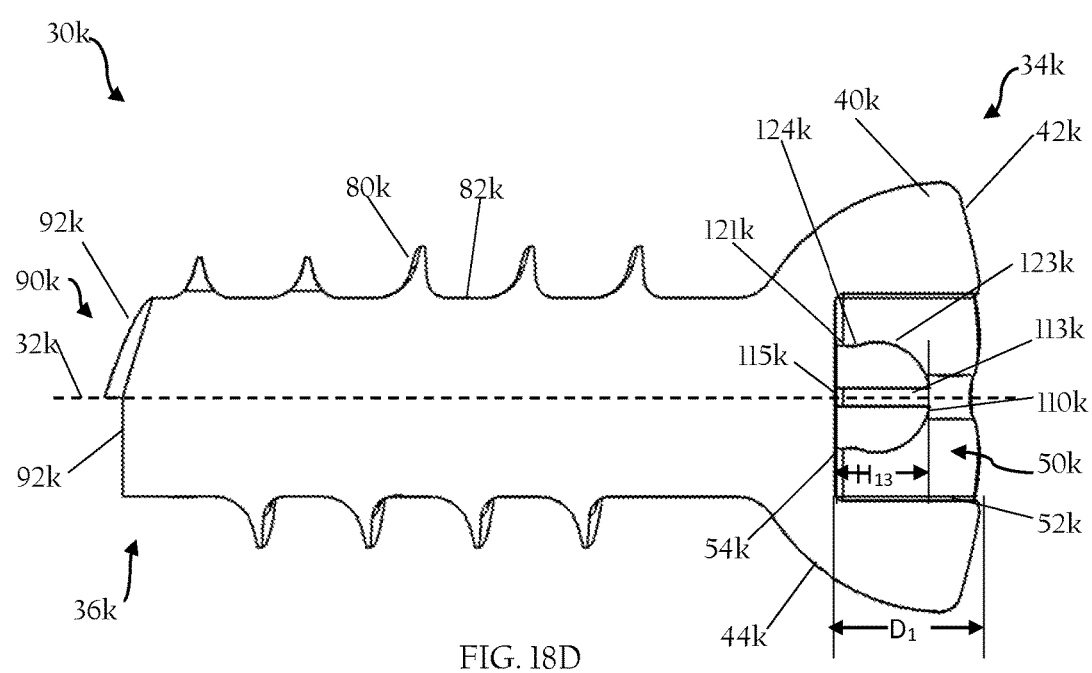

Although not shown, it will be appreciated that the screwdriver 150 for use with the screw 30*k* of FIGS. 18A and 18B could be configured to cooperate with the screw 30*k* in a similar manner to how the screwdriver 150 cooperates with the screw 30 of FIGS. 2-4. In particular, with the screw 30*k* of FIGS. 18A and 18B, the lobes 174 of the pilot 170 are sized and contoured to have a slip fit with the spaces 68*k* in the head 40*k* of the screw 30*k*. The spaces 176 between the lobes 174 are sized and contoured to form a slip fit with the lobes 66*k* of the screw 30*k*. Consequently, the portion 182 has a hexalobe axial cross-section similar to the hexalobe axial cross-section of the recess 50*k*.

For the corresponding driving tool, the inner surface 189 of the opening 190 can be sized and contoured to engage with and/or form a friction fit with the projection 110*k* on the screw 30*k*. More specifically, the inner surface 189 may have a circular axial cross-section and a frustoconical shape that tapers inwardly in a direction extending from the axial end surface 168 towards the body 160. The axial cross-section and taper of the inner surface 189 are such that the inner surface and projection 110*k*, more specifically the spherical second portion 123*k*, can engage with and/or form a provisional engagement and/or friction fit with one another within the recess 190. For example, the inner surface 189 may be sized to deflect the portions of the projection 110*k* inward towards the axis 32*k* such that the resistance of the projection portions to the deflection enhances the provisional engagement and/or friction fit between the projection and the inner surface. The undercut 124*k* facilitates deflection of the projection 110*k* portions by the inner surface 189 and therefore further helps to enhance the provisional engagement and/or friction fit. The inner surface 189 may be configured to allow the pilot 170 to abut the inner end surface 54*k* or the pilot may be spaced from the inner surface when the provisional engagement and/or friction fit is formed. Alternatively, the inner surface 189 may include a notched or detent section within the opening 190, with a portion of the opening 190 sized to deflect the portions of the projection 110*k* inward towards the axis 32*k*. When compressed, portions of the projection 110*k* can create a force directed radially outward, when engaging with the pilot, potentially creating a higher provisional engagement force. This action can allow the deflected projection portions to "snap back" or resume some portion of their original position when fully seated within the opening 190 (with some portion of the second portion 123K sitting within the detent or groove and/or desirably provisionally mechanically "locking" the fastener to the driving tool. If desired, this "locking" action could be accompanied by an audible "click" and/or tactile feedback that such provisional engagement has occurred. Furthermore, the distinct portions in combination with the projection undercut 124*k* can significantly increase the provisional engagement force, if desired.

If desired, a projection may extend from the axial end surface 191 and be sized and shaped for cooperating with the passage 113*k* in the screw 30*k* to help align the screwdriver 150 and screw 30*k* along the axes 32*k*, 152. To this end, this projection may have an x-shaped, t-shaped or l-shaped axial cross-section and be centered on the axis 152. In other embodiments, the projection might selectively extend into the passage 113*k* and desirably interfere with deflection or other movement of the projections, and in some embodiments might form a "locking feature" which selective locks and/or unlocks the provisional engagement feature between the screw and the driving tool.

Referring to FIGS. 19A through 19D, another embodiment of a fastener could incorporate a projection 110*m* which comprises a first portion 121*m* having a cylindrical shape and a second portion 123*m* having a generally frustoconical shape. The first portion 121*m* can extend along the axis 32*m* away from the inner end surface 54*m*. The second portion 123*m* can extend along the axis 32*m* from the first portion 121*m* away from the inner end surface 54*m*. The largest axial cross-section of the second portion 123*m* may be larger than the axial cross-section of the first portion 121*m*, thereby forming an undercut 124*m* between the first and second portions, with the undercut being flat, angled and/or rounded, as desired. The height $H_{14}$ of the projection 110*m* measured from the inner end surface 54*m* to the proximal extent is less than the depth $D_1$ of the recess 50*m*, although the height $H_{14}$ of the projection 110*m* may be equal to or greater than the depth $D_1$ of the recess 50*m* (not shown).

The passage 113*m* in the projection 110*m* on the screw 30*m* can have an x-shaped axial cross-section and extend from the proximal extent towards the second end 36*m* of the screw 30*m*. The passage 113*m* can extend substantially parallel to the axis 32*m* while extending towards the second end 36*m* of the screw 30*m*. The passage 113*m* terminates at an inner end surface 115*m* within the projection 110*m*, although the inner end surface may alternatively be positioned within the body 80*m* or in other locations (not shown). The inner end surface 115*m* may therefore be substantially coplanar with the inner end surface 54*m* or spaced axially from the inner end surface in the proximal or distal direction along the axis 32*m*.

As shown, the passage 113*m* extends the entire length of the projection 110*m*, although the passage may extend through less of the projection, if desired. The passage 113*m* extends radially from the axis 32*m* through the entire projection 110*m* and divides the projection into four distinct portions. It will be appreciated that the passage 113*m* may be configured to divide the projection 110*m* into more or fewer distinct portions. In any case, the passage 113*m* can be centered on the axis 32*m* and allows the portions of the projection 110*m* to radially deflect relative to the axis and one another.

Figure 19A:
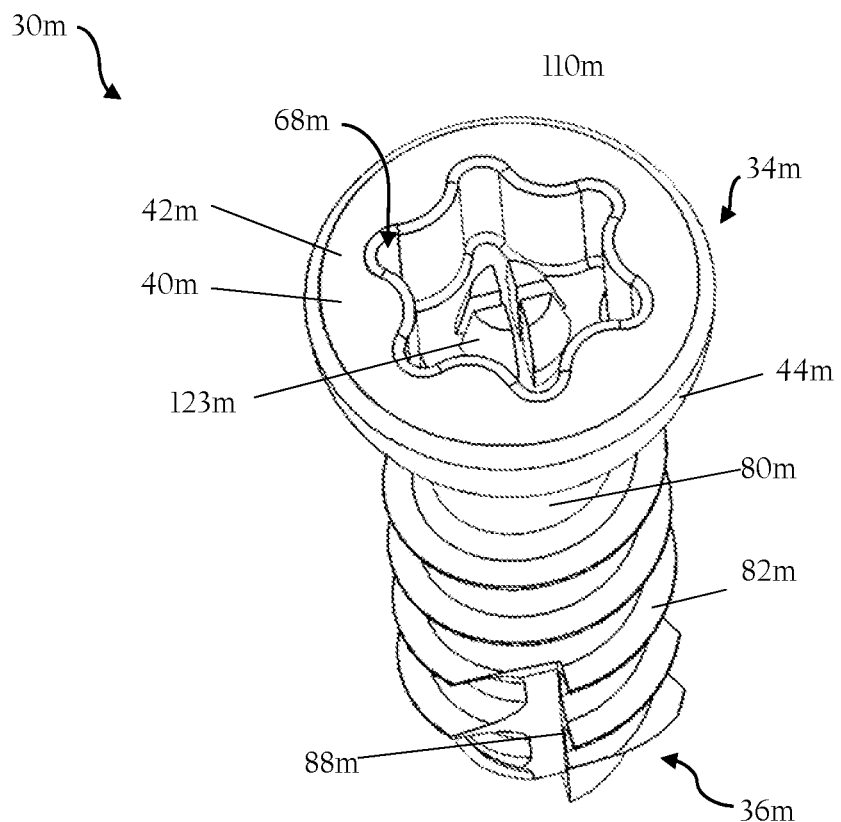
FIGS. 19A through 19D illustrate various views of a fastener having another alternative configuration.
Figure 19B:
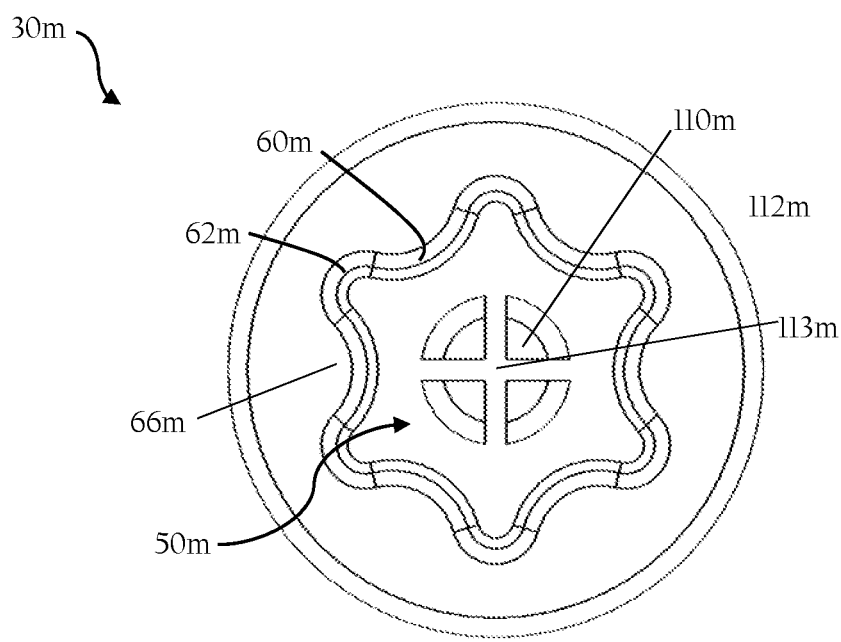
Figure 19C:
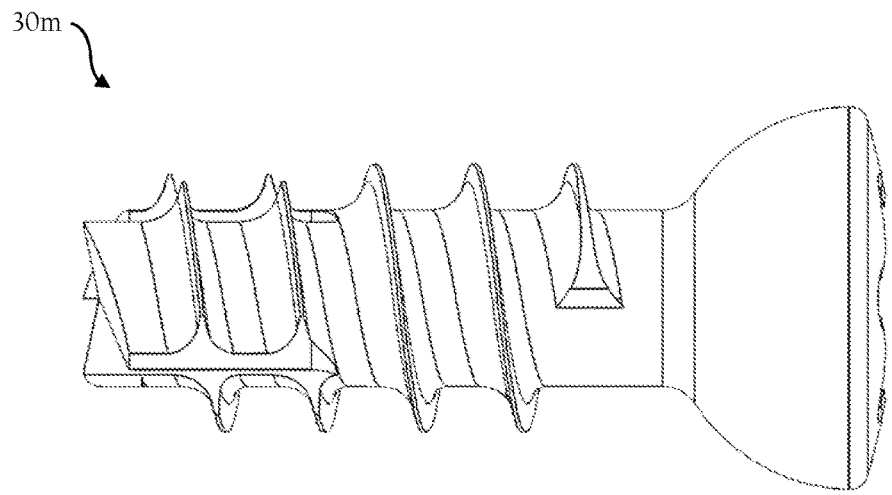
Figure 19D:
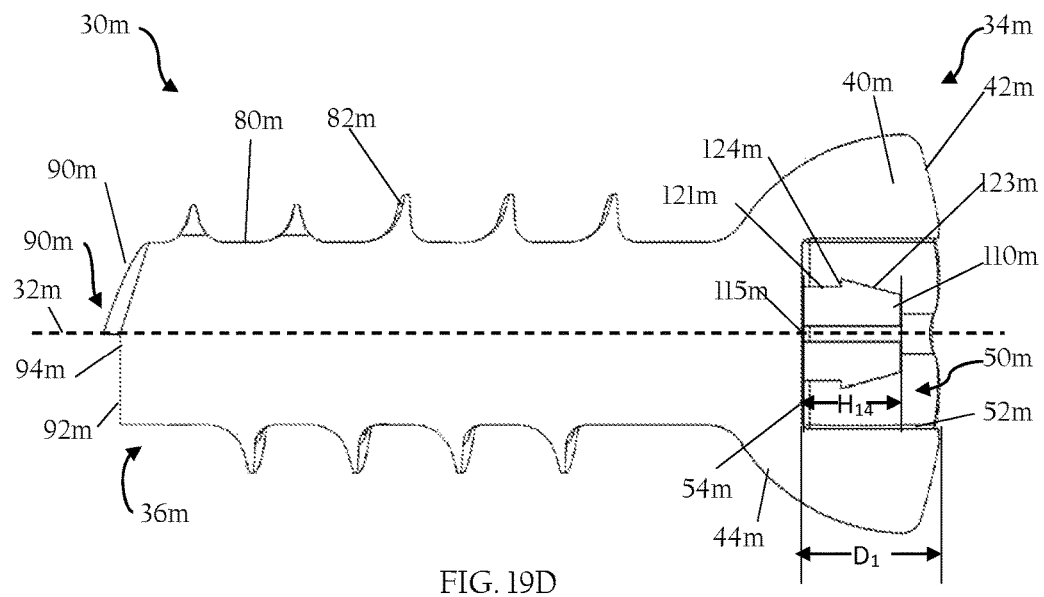
Figure 20A:
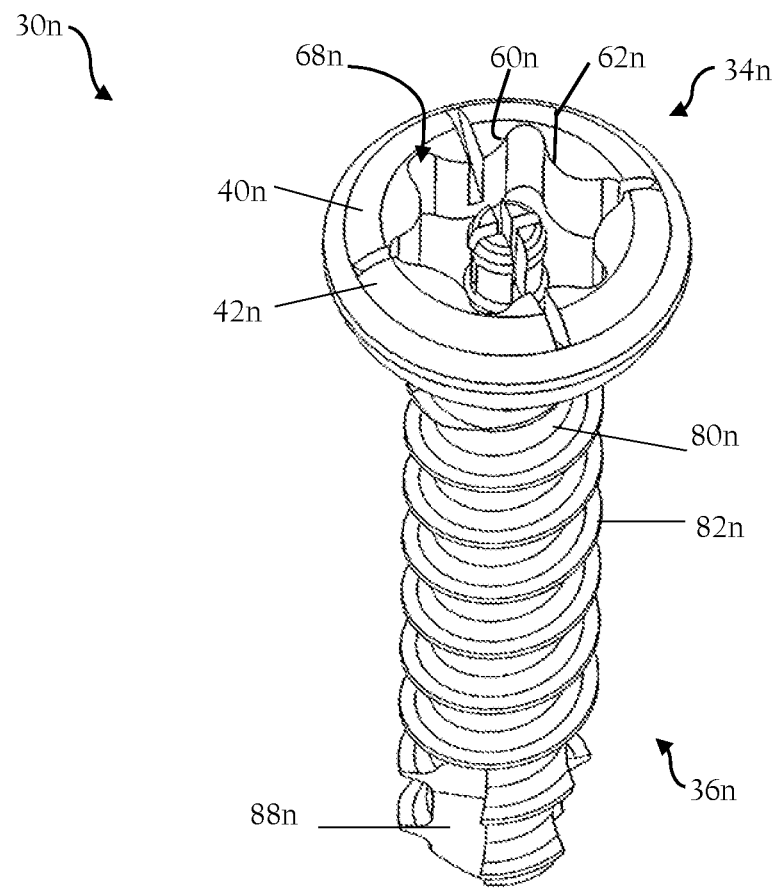
FIGS. 20A through 20D illustrate various views of a fastener having another alternative configuration.
Figure 20B:
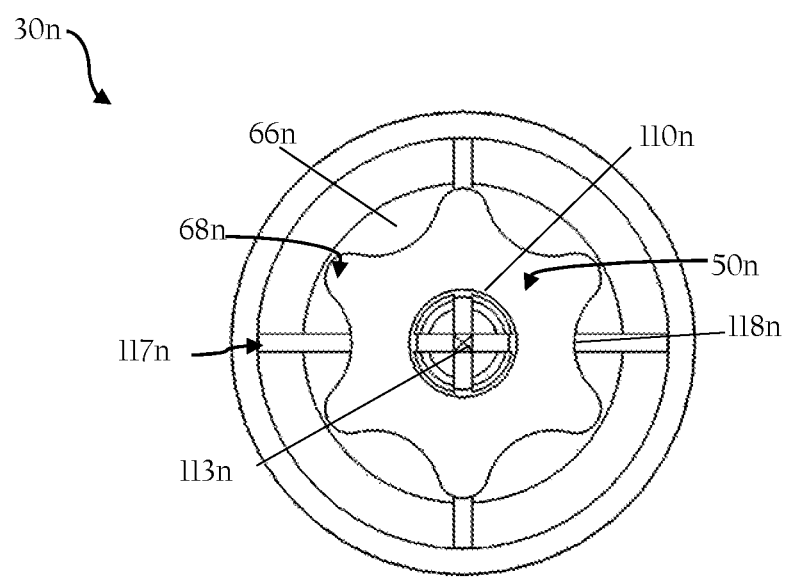
Figure 20C:
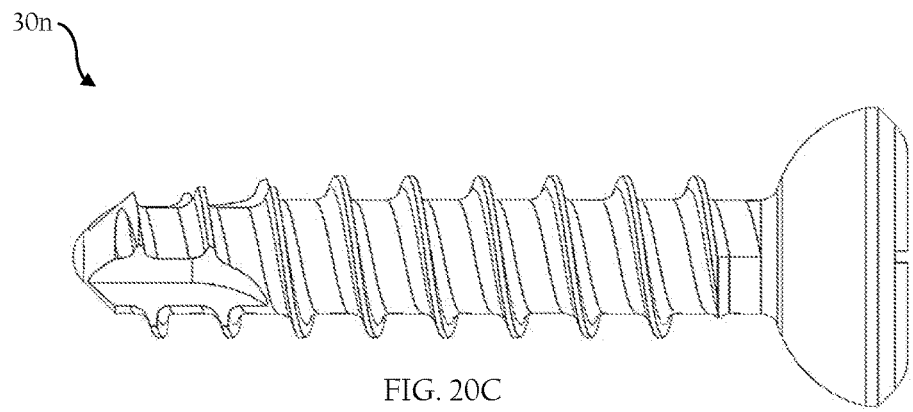
Figure 20D:
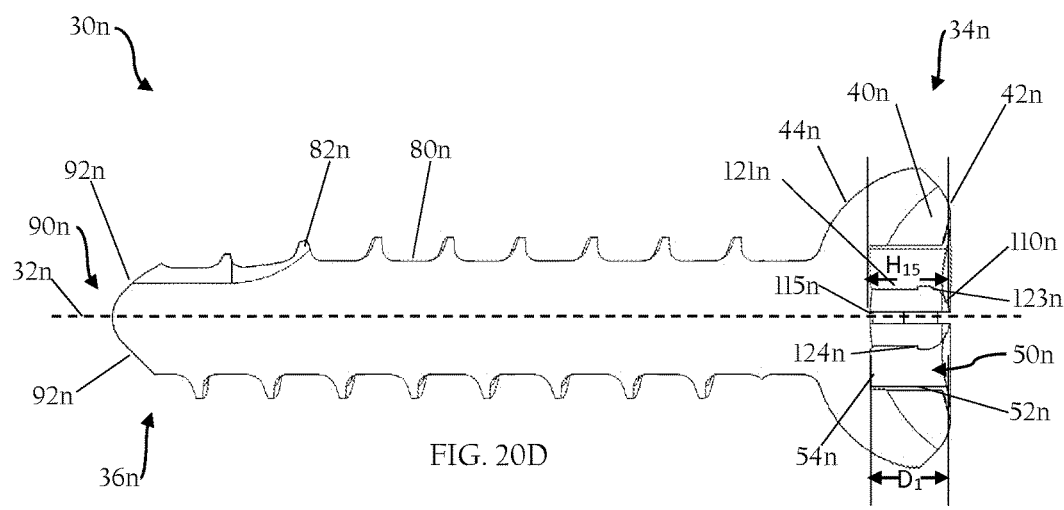
Figure 21A:
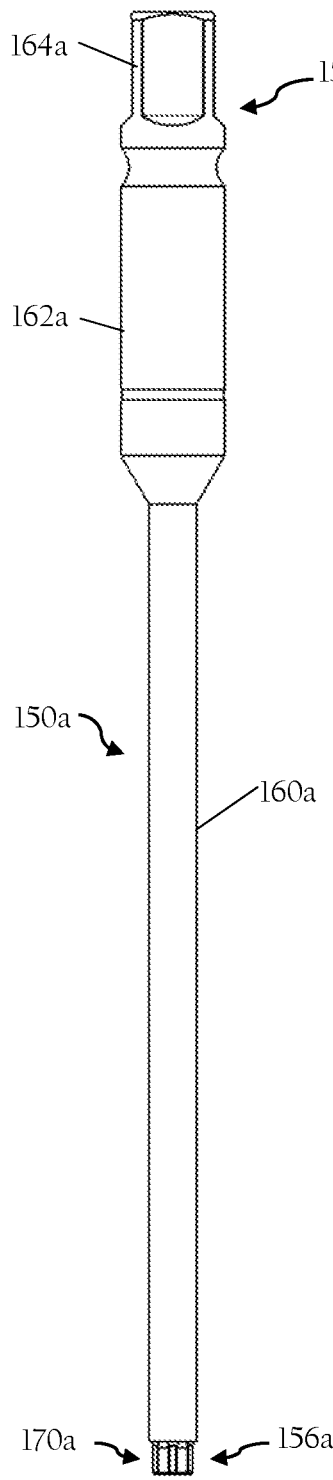
FIGS. 21A through 21 C illustrate various views of another exemplary embodiment of a driving tool for use with various fasteners of the present invention.
Figure 21B:
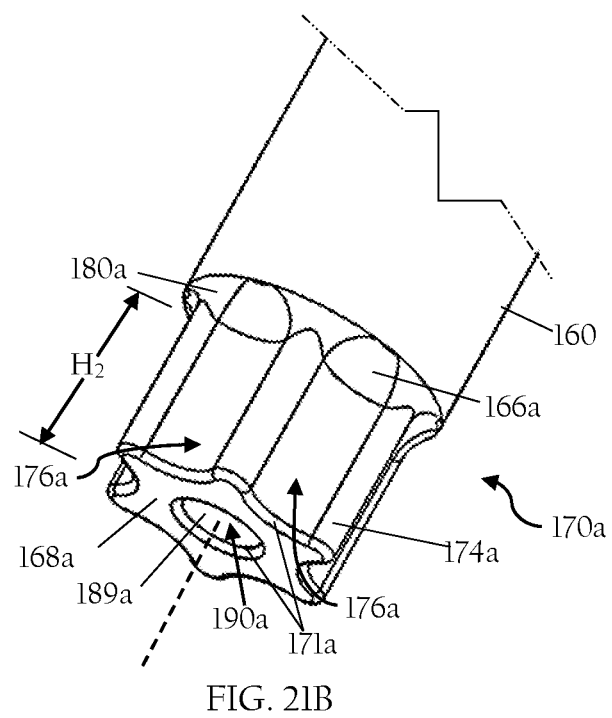
Figure 21C:
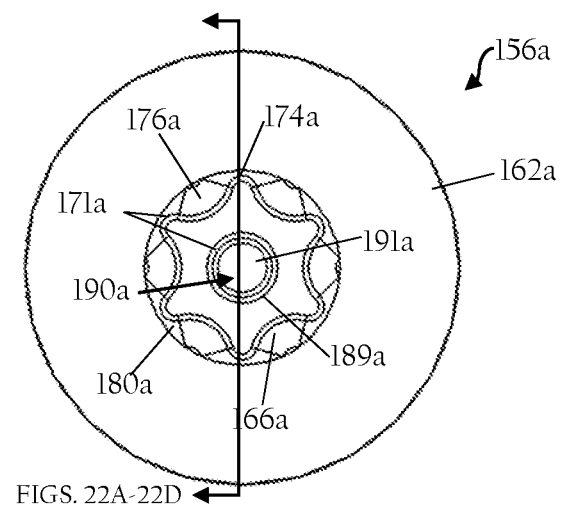

Although not shown, it will be appreciated that the screwdriver 150 for use with the screw 30*m* of FIGS. 19A and 19B could be configured to cooperate with the screw 30*m* in a similar manner to how the screwdriver 150 cooperates with the screw 30 of FIGS. 2-4. In particular, with the screw 30*m* of FIGS. 19A and 19B, the lobes 174 of the pilot 170 could be sized and contoured to have a slip fit with the spaces 68*m* in the head 40*m* of the screw 30*m*. The spaces 176 between the lobes 174 could be sized and contoured to form a slip fit with the lobes 66*m* of the screw 30*m*. Consequently, the portion 182 has a hexalobe axial cross-section similar to the hexalobe axial cross-section of the recess 50*m*.

The inner surface 189 of the opening 190 of a pilot 170 of a corresponding driving tool could be sized and contoured to engage with and/or form a friction fit with the projection 110*m* on the screw 30*m*. More specifically, the inner surface 189 may have a circular axial cross-section and a frustoconical shape that tapers inwardly in a direction extending from the axial end surface 168 towards the body 160. The axial cross-section and taper of the inner surface 189 could be such that the inner surface and projection 110*m* (more specifically, the frustoconical second portion 123*m*) could form a provisional engagement and/or friction fit with one another within the recess 190. For example, the inner surface 189 may be sized to deflect the portions of the projection 110*m* inward towards the axis 32*m* such that the resistance of the projection portions to the deflection enhances the provisional engagement and/or friction fit between the projection and the inner surface (with the second portions 123*m* of the projection desirably urging the portions slightly inward as the opening 190 slides over the projection). Once within the opening 190, the undercut 124*m* can rest against the walls of the opening 190 and/or engage with a corresponding ridge, notch or depression within the opening 190, or could merely facilitate deflection of the projection 110*m* portions by the inner surface 189 and therefore further help to enhance the mechanical and/or frictional resistance of the screw to removal from the tool. Furthermore, the deflection of the projection 110*m* portions may provide an audible "click" or tactile feedback that the provisional engagement has occurred. The inner surface 189 may be configured to allow the pilot 170 to abut the inner end surface 54*m* or the pilot may be spaced from the inner surface when the provisional engagement and/or friction fit is formed.

If desired, a projection might extend from the axial end surface 191 of the opening 190 and be sized and shaped for cooperating with the passage 113*m* in the screw 30*m* to help align the screwdriver 150 and screw 30*m* along the axes 32*m*, 152. To this end, this projection may have an x-shaped axial cross-section and/or be centered on the axis 152. In other embodiments, the projection might selectively extend into the passage 113*m* and desirably interfere with deflection or other movement of the projections, and in some embodiments might form a "locking feature" which selective locks and/or unlocks the provisional engagement feature between the screw and the driving tool.

Referring to FIGS. 20A through 20D, another embodiment of a fastener could incorporate a projection 110*n* which comprises a first portion 121*n* having a cylindrical shape and a second portion 123*n* having a generally hemispherical shape. The first portion 121*n* can extend along the axis 32*n* away from the inner end surface 54*n*. The second portion 123*n* can extend along the axis 32*n* from the first portion 121*n* away from the inner end surface 54*n*. The largest axial cross-section of the second portion 123*n* may be larger than the axial cross-section of the first portion 121*n*, thereby forming a lip or undercut section 124*n* between the first and second portions, with the undercut being rounded, curved, flat, and/or angled (either positive and/or negative and/or reverse angles are contemplated), as desired. The height $H_{14}$ of the projection 110*n* measured from the inner end surface 54*n* to the proximal extent can be less than the depth D1 of the recess 50*m*, although the height $H_{15}$ of the projection 110*m* may be equal to or greater than the depth D1 of the recess 50*n* (not shown).

The passage 113*n* in the projection 110*n* on the screw 30*n* can have an x-shaped axial cross-section and extend from the proximal extent towards the second end 36*n* of the screw 30*n*. The passage 113*n* can extend substantially parallel to the axis 32*n* while extending towards the second end 36*n* of the screw 30*n*. The passage 113*n* can terminate at an inner end surface 115*n* within the projection 110*n*, although the inner end surface may alternatively be positioned within the body 80*n* or in other locations (not shown). The inner end surface 115*n* may therefore be substantially coplanar with the inner end surface 54*n* or spaced axially from the inner end surface in the proximal or distal direction along the axis 32*n*.

As shown, the passage 113*n* extends the entire length of the projection 110*n*, although the passage may extend through less of the projection, if desired. The passage 113*n* extends radially from the axis 32*n* through the entire projection 110*n* and divides the projection into four distinct portions. It will be appreciated that the passage 113*n* may be configured to divide the projection 110*n* into more or fewer distinct portions. In any case, the passage 113*n* can be centered on the axis 32*n* and allows the portions of the projection 110*n* to radially deflect relative to the axis and one another.

Although not shown, it will be appreciated that the screwdriver 150 for use with the screw 30*n* of FIGS. 20A through 20D could be configured to cooperate with the screw 30*n* in a similar manner to how the screwdriver 150 cooperates with the screw 30 of FIGS. 2-4. In particular, with the screw 30*n* of FIGS. 20A through 20D, the lobes 174 of the pilot 170 could be sized and contoured to have a slip fit with the spaces 68*n* in the head 40*n* of the screw 30*n*. The spaces 176 between the lobes 174 could be sized and contoured to form a slip fit with the lobes 66*n* of the screw 30*n*. Consequently, the portion 182 could have a hexalobe axial cross-section similar to the hexalobe axial cross-section of the recess 50*n*.

The inner surface 189 of the opening 190 in a pilot 170 of a corresponding driving tool could be sized and contoured to engage with and/or form a friction fit with the projection 110*n* on the screw 30*n*. More specifically, the inner surface 189 may have a circular axial cross-section and a cylindrical or frustoconical shape (i.e., that tapers inwardly in a direction extending from the axial end surface 168 towards the body 160) that desirably includes features that can engage with the projection. The axial cross-section and smooth walls or taper of the inner surface 189 could be such that the inner surface and projection 110*n* (more specifically, the frustoconical second portion 123*n*) could engage with and/or form a friction fit with one another within the recess 190. For example, the inner surface 189 may simply be sized to deflect the portions of the projection 110*n* inward towards the axis 32*n* such that the resistance of the projection portions to the deflection enhances the provisional engagement and/or friction fit between the projection and the inner surface (with the second portions 123*n* of the projection desirably urging the portions slightly inward as the opening 190 slides over the projection). Once within the opening 190, the undercut 124*n* can rest against the walls of the opening 190 and/or engage with a corresponding ridge, notch or depression within the opening 190, or could merely facilitate deflection of the projection 110*n* portions by the inner surface 189 and therefore further help to enhance the mechanical and/or frictional resistance of the screw to removal from the tool. The inner surface 189 may be configured to allow the pilot 170 to abut the inner end surface 54*n* or the pilot may be spaced from the inner surface when the provisional engagement and/or friction fit is formed.

If desired, a projection might extend from the axial end surface 191 within the opening 190 and be sized and shaped for cooperating with the passage 113*n* in the screw 30*n* to help align the screwdriver 150 and screw 30*n* along the axes 32*n*, 152. To this end, this projection may have an x-shaped axial cross-section and/or be centered on the axis 152. In other embodiments, the projection might selectively extend into the passage 113*n* and desirably interfere with deflection or other movement of the projections, and in some embodiments might form a "locking feature" which selective locks and/or unlocks the provisional engagement feature between the screw and the driving tool.

One particular utilitarian feature of the embodiments of FIGS. 14A through 15D and 17A through 20D is the ability of the various screw embodiments to accommodate a wide variety of driving tool configurations, if desired. For example, the placement of notches 117*n* in the walls of the head 42*n* could accommodate the "tangs" or driving surfaces of a Phillip's Head screwdriver and/or the blades of a flathead screwdriver (which can also be accommodated by the passage 113*n*, while the remainder of the recess could accommodate a hexalobular driver, as previously described. Alternatively, the projections of the various embodiments might also incorporate features capable of accommodating different types of socket wrenches, if desired. If desired, the walls features of the recess could be altered to accommodate both a hexalobular driver and a hexagonal driver. By combining various driving features such as those described herein, the present fasteners could accommodate a variety of driving tools, and potentially simplify the tool requirements for a user of the system.

In other alternative embodiments, the various provisional retention features described herein could be incorporated into other types of fasteners, including fasteners having driving surfaces formed on an outside of the fastener head (i.e., a hex-head bolt driven by a socket driver). In various embodiments, the fastener head could incorporate a head with a recess formed therein, and a projection of other feature at least partially disposed within the recess that provisionally engages with a centrally-formed opening in the driving tool (in a manner similar to the embodiments previously described), and the inner walls of the socket driver engaging the driving surfaces on the outside of the bolt head.

FIGS. 21A through 22D depict various exemplary configurations for a driving tool or screwdriver having a driving tip with a pilot opening formed therein. These figures depict a variety of alternative configurations that incorporate various provisional engagement features for the fastening tool. In these figures, similar components for many features to those found in FIGS. 5-6B have been given the same reference numeral with the added suffix "a", "b", "c", "d", and "e", respectively. Although not shown or specifically described in many embodiments, it should be understood that virtually any combination of the various fastening tool features described herein could be combined, and the tool would desirably be appropriately contoured, shaped and/or sized to the shapes of the recess and/or projection, which could include identical configurations or configurations capable of engaging with corresponding features in each of the alternative configurations of FIGS. 8A-20D. In various described embodiments, a corresponding pilot inner surface and screw head projection could be designed to provide appropriate provisional engagement structures and their related relationships with each other, such as a friction fit, to provide similar or the same advantages as the screw 30 and screwdriver 150 of FIGS. 1-6B.

Figure 22A:
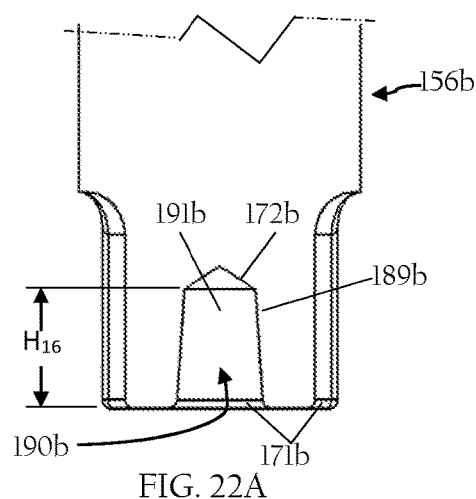
FIG. 22A depicts a cross-sectional view of one alternative embodiment of a pilot of a driving tool taken along line 22A-22A of FIG. 21C.

FIG. 22A depicts a cross-sectional view of one exemplary embodiment of a driving tool pilot incorporating an opening 190*b* for accommodating a projection of a fastener, such as those described in the various embodiments herein. In this embodiment, the opening 190*b* comprises a generally frustoconical shape 189*b*, which may be formed in the shape of a Morse taper or other known configurations. Desirably, the walls of the opening will engage with and retain a corresponding projection of a fastener, which in various embodiments could incorporate corresponding tapered walls, cylindrical walls and/or deflectable projections. Also depicted are tapered or rounded portions 171*b*, which desirably facilitate placement of the tool onto the projections and/or into the recess of the fastener. A space 172*b* can be included to simplify machining of the opening 190*b* by known techniques.

Figure 22B:
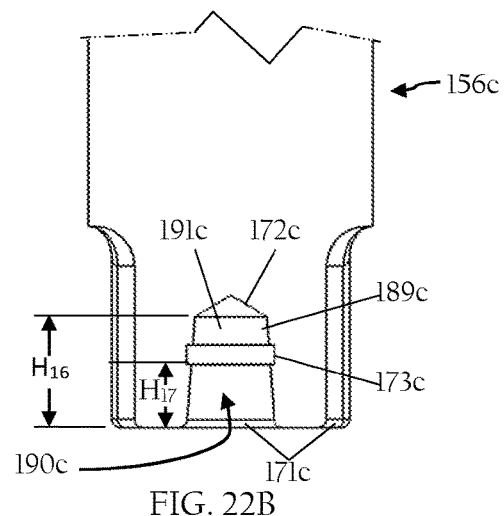
FIG. 22B depicts a cross-sectional view of another alternative embodiment of a pilot of a driving tool taken along line 22B-22B of FIG. 21C.

FIG. 22B depicts a cross-sectional view of another exemplary embodiment of a driving tool pilot incorporating an opening 190*c* for accommodating a projection of a fastener, such as those described in the various embodiments herein. In this embodiment, the opening 190*c* comprises a generally frustoconically shaped opening 189*c*, which may be formed in the shape of a Morse taper or other known configurations. The opening further includes a recessed or notched portion 173*c*, which desirably engages with a corresponding projection of a fastener, which in various embodiments could incorporate corresponding tapered walls, cylindrical walls and/or deflectable projections with overhanging lips, etc. Also depicted are tapered or rounded portions 171*c*, which desirably facilitate placement of the tool onto the projections and/or into the recess of the fastener. A space 172*c* can be included to simplify machining of the opening 190*c* by known techniques.

Figure 22C:
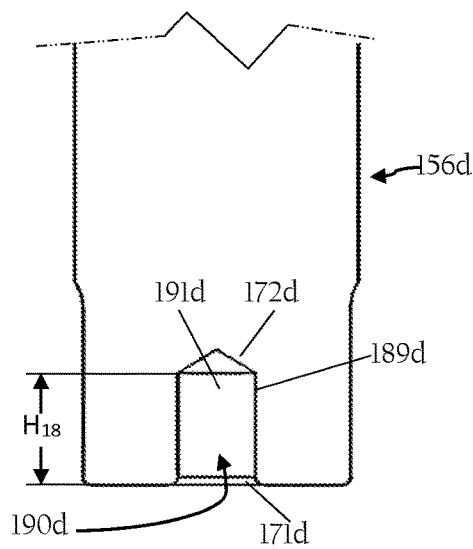
FIG. 22C depicts a cross-section view of another alternative embodiment of a pilot of a driving tool taken along line 22C-22C of FIG. 21C.

FIG. 22C depicts a cross-sectional view of another alternative embodiment of a driving tool pilot incorporating an opening 190*c* for accommodating a projection of a fastener, such as those described in the various embodiments herein. In this embodiment, the opening 190*c* comprises a generally cylindrical shape 189*d* with a terminal space 172*c*. Desirably, the walls of the opening will engage with and retain a corresponding projection of a fastener, which in various embodiments could incorporate corresponding tapered walls, cylindrical walls and/or deflectable projections. Also depicted are tapered or rounded portions 171*d*, which desirably facilitate placement of the tool onto the projections and/or into the recess of the fastener.

Figure 22D:
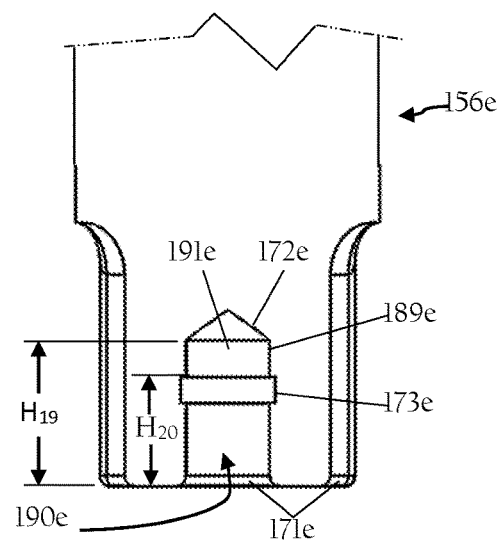
FIG. 22D depicts a cross-section view of another alternative embodiment of a pilot of a driving tool taken along line 22D-22D of FIG. 21C.

FIG. 22D depicts a cross-sectional view of another exemplary embodiment of a driving tool pilot incorporating an opening 190*e* for accommodating a projection of a fastener, such as those described in the various embodiments herein. In this embodiment, the opening 190*e* comprises a generally frustoconically shaped opening 189*e*. The opening further includes a recessed or notched portion 173*e*, which desirably engages with a corresponding projection of a fastener, which in various embodiments could incorporate corresponding tapered walls, cylindrical walls and/or deflectable projections with overhanging lips, etc. Also depicted are tapered or rounded portions 171*e*, which desirably facilitate placement of the tool onto the projections and/or into the recess of the fastener. A space 172*e* can be included to simplify machining of the opening 190*e* by known techniques.

Another particularly useful feature of the various embodiments disclosed herein is the ability of the system to be utilized with non-ferrous and/or non-magnetic materials (i.e., fasteners and/or driving tools). Unlike magnetic retention bits, which require ferrous or magnetic screws, the features of the present invention can be utilized with virtually any materials (i.e., stainless steel, titanium, plastics, ceramics, etc.) and can be used in virtually any environment, even where the use of ferrous materials and/or magnetic devices may be undesirable and/or prohibited (i.e., in high-energy electrical environments and/or near high-strength magnets such as contained in Magnetic Resonance Imaging machines).

In various embodiments, the dimensions, shapes and tolerancing of the various fasteners and driving tools described herein can be particularized to a specific application. For example, if a greater amount of retention force is desired for the provisional engagement feature, the taper of the opening can be altered to increase the holding strength. Conversely, if less holding force is desired, the taper of the opening can reduced and/or increased accordingly. Similarly, the depths of the opening and/or length of the projection can be altered, with greater dimensions typically increasing the holding strength. Similarly, the relative shapes and/or sizes of the projection(s) and/or opening in the pilot could be altered to provide greater or lesser holding forces. In other embodiments, the size, shape, surface features, thickness and/or stiffness of the projections could be altered, with commensurate alterations to the provisional holding strength of the fastener to the tool. In other embodiments, the angle of the undercut on a projection and/or inner wall of a notch in the tool opening can be altered (i.e., 90°, 60°, 45°, etc.) to desirably alter the holding force.

The embodiments herein describe engagement features for the various fasteners and tools that are relatively inexpensive and easily formed, and are particularly robust in their applications. For example, the opening in the pilot of the driving tool can be formed via a simple drilling and/or machining operation, and the simplified design is highly resistant to fatigue and/or failure during the repeated application and/or removal of numerous fasteners accomplished with a single driving tool. Moreover, the projection(s) incorporated into the recess of each fastener are unlikely to fracture and/or failure (i.e., due to material fatigue) during the limited number of times that the fastener is expected to be attached and/or removed from the work piece, and thus the opportunity for failure of these components is also greatly reduced. Moreover, the ability to incorporate the various features into many existing fastener and driving tool designs greatly enhances the cost-effectiveness and utility of the various features described herein.

The screws and screwdrivers of the present invention are advantageous in that the provisional engagement and/or friction fit between the projection and pilot reliably retains the screw on the screwdriver without manual assistance. Furthermore, the limited number of sides on the projection that cooperate with the recess in the screwdriver help to ensure a reliable, repeatable connection therebetween. More specifically, by limiting the number of cooperating surfaces between the screw projection and screwdriver recess forming the provisional engagement and/or friction fit, machining tolerances can be more reliably held to form a precise provisional engagement and/or friction fit. Conversely, the slip fit connection between the pilot and inner surface of the recess can be made with more forgiving tolerances, which is beneficial given the increased number of cooperating surfaces between the pilot and inner surface of the screw, and in various embodiments the disclosed design features can provide an adequate provisional engagement force even where sloppy or poor manufacturing and/or tolerancing of engagement features exists. Moreover, embodiments that provide a projection on the screw that does not extend out of the recess advantageously can reduce the risk of projection breakage and minimize interaction between the screw and the surrounding structure.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein. For example, it will be understood that a screw in accordance with the present invention may include any combination of axially extending inner surface 52-52n and projections 110-100n shown and/or described herein.

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

The various headings and titles used herein are for the convenience of the reader, and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A fastener extending along a longitudinal axis and having a proximal end and a distal end, the fastener comprising:
    a head located at the proximal end and a shaft extending distally from the head, the shaft having an axial width that is less than an axial head width of the head;
    the head having a proximal surface with a recess formed therein, the recess extending from the proximal surface towards the distal end of the fastener and terminating at an inner recessed surface;
    the recess including an inner wall extending from the proximal surface to the inner recessed surface, at least a portion of the inner wall including a plurality of engagement surfaces for engaging a driving tool; and
    extending proximally from the inner recessed surface are a plurality of fingers, the plurality of fingers positioned proximate to a longitudinal center of the recess, each finger including a longitudinally extending finger body with a proximal finger head, at least a portion of each proximal finger head including an outwardly protruding portion.

2. The fastener of claim 1, wherein each of the proximal finger heads includes a rounded proximal portion.

3. The fastener of claim 1, wherein each of the proximal finger heads includes a tapered proximal portion.

4. The fastener of claim 3, wherein each of the proximal finger heads is spaced apart from each other.

5. The fastener of the claim 4, wherein each of the proximal finger heads is located within the recess.

6. The fastener of claim 5, wherein at least a portion of the proximally extending fingers flexes when the fastener engages the driving tool.

7. The fastener of the claim 1, wherein a proximal surface of each of the proximal finger heads is positioned flush with the proximal surface of the head.

8. The fastener of the claim 1, wherein at least a portion of each of the proximal finger heads is located outside of the recess.

9. A fastener extending along a longitudinal axis and having a proximal end and a distal end, the fastener comprising:
- a head located at the proximal end and a threaded shaft extending distally from the head, the threaded shaft having a transverse shaft width that is less than a transverse head width of the head;
- the head having a proximal surface with a recess formed therein, the recess having a transverse recess width that is less than a major diameter of the threaded shaft, the recess extending from the proximal surface towards the distal end of the fastener and terminating at an inner recessed surface;
- the recess including an inner wall extending from the proximal surface to the inner recessed surface, at least a portion of the inner wall including a plurality of engagement surfaces for engaging a driving tool; and
- extending proximally from the inner recessed surface are at least two projections, each projection including a longitudinally extending flexible projection body with a proximal projection head, at least a portion of the proximal projection head including an undercut portion facing towards the inner wall;
- wherein at least a portion of the flexible projection body flexes when the fastener engages the driving tool.

10. The fastener of claim 9, wherein the proximal projection head is positioned within the recess.

11. A screw extending along a longitudinal axis and having a proximal end and a distal end, the screw comprising:
- a head located at the proximal end and a shaft extending distally from the head, the shaft having a transverse shaft width that is less than a transverse head width of the head, the shaft having an externally facing thread for securing the screw into a structure;
- the head having a proximal surface with a recess formed therein, the recess having a transverse recess width that is less than an outer diameter of the externally facing thread of the shaft, the recess extending from the proximal surface towards the distal end of the screw and terminating at an inner recessed surface;
- the recess including an inner wall extending from the proximal surface to the inner recessed surface, at least a portion of the inner wall including a plurality of lobes for engaging a driving tool; and
- extending from the inner recessed surface are a plurality of proximally extending fingers, each finger including a longitudinally extending finger body with a proximal finger head, at least a portion of each proximal finger head including an undercut portion.

12. The screw of claim 11, wherein each of the proximal finger heads includes a rounded proximal portion.

13. The screw of claim 11, wherein each of the proximal finger heads includes a tapered proximal portion.

14. The screw of claim 13, wherein each of the proximal finger heads is spaced apart from each other.

15. The screw of the claim 14, wherein each of the proximal finger heads is located within the recess.

16. The screw of the claim 14, wherein a proximal surface of each of the proximal finger heads is positioned flush with the proximal surface of the head.

17. The screw of claim 14, wherein at least a portion of the proximally extending fingers flexes when the screw engages the driving tool.

18. The screw of claim 17, wherein the plurality of proximally extending fingers comprise at least four proximally extending fingers, with the at least four proximally extending fingers spaced equally around a longitudinal center of the recess.

19. The screw of the claim 11, wherein at least a portion of each of the proximal finger heads is located outside of the recess.

20. The screw of claim 11, wherein the shaft is cannulated along the longitudinal axis.

* * * * *